(12) United States Patent
Zhang et al.

(10) Patent No.: US 8,968,940 B2
(45) Date of Patent: *Mar. 3, 2015

(54) REDOX SHUTTLES FOR HIGH VOLTAGE CATHODES

(75) Inventors: Lu Zhang, Lisle, IL (US); Zhengcheng Zhang, Naperville, IL (US); Khalil Amine, Oak Brook, IL (US); Zonghai Chen, Bolingbrook, IL (US)

(73) Assignee: UChicago Argonne, LLC, Chicago, IL (US)

( * ) Notice: Subject to any disclaimer, the term of this patent is extended or adjusted under 35 U.S.C. 154(b) by 915 days.

This patent is subject to a terminal disclaimer.

(21) Appl. No.: 13/114,468

(22) Filed: May 24, 2011

(65) Prior Publication Data

US 2011/0294018 A1 Dec. 1, 2011

Related U.S. Application Data

(60) Provisional application No. 61/348,050, filed on May 25, 2010.

(51) Int. Cl.
| | |
|---|---|
| *H01M 6/16* | (2006.01) |
| *C07F 9/09* | (2006.01) |
| *C07F 9/40* | (2006.01) |
| *H01M 10/0525* | (2010.01) |
| *H01M 10/0567* | (2010.01) |
| *H01M 10/42* | (2006.01) |
| *H01M 10/0568* | (2010.01) |
| *H01M 10/0569* | (2010.01) |

(52) U.S. Cl.
CPC .............. *C07F 9/093* (2013.01); *C07F 9/4006* (2013.01); *C07F 9/4075* (2013.01); *C07F 9/4084* (2013.01); *H01M 10/0525* (2013.01); *H01M 10/0567* (2013.01); *H01M 10/4235* (2013.01); *H01M 10/0568* (2013.01); *H01M 10/0569* (2013.01); *H01M 2200/00* (2013.01); *Y02E 60/122* (2013.01)
USPC ........................................................ 429/338

(58) Field of Classification Search
None
See application file for complete search history.

(56) References Cited

U.S. PATENT DOCUMENTS

| | | | |
|---|---|---|---|
| 5,526,599 | A | 6/1996 | Roussel |
| 5,709,968 | A | 1/1998 | Shimizu |
| 5,763,119 | A | 6/1998 | Adachi |
| 5,858,324 | A | 1/1999 | Dahn et al. |
| 5,858,573 | A | 1/1999 | Abraham et al. |
| 5,882,812 | A | 3/1999 | Visco et al. |
| 5,900,385 | A | 5/1999 | Dahn et al. |
| 6,004,698 | A | 12/1999 | Richardson et al. |
| 6,045,952 | A | 4/2000 | Kerr et al. |
| 6,143,268 | A | 11/2000 | Dahn et al. |
| 6,203,944 | B1 | 3/2001 | Turner et al. |
| 6,255,017 | B1 | 7/2001 | Turner |
| 6,387,571 | B1 | 5/2002 | Lain et al. |
| 6,436,578 | B2 | 8/2002 | Turner et al. |
| 6,503,662 | B1 | 1/2003 | Hamamoto et al. |
| 6,664,004 | B2 | 12/2003 | Krause et al. |
| 6,680,145 | B2 | 1/2004 | Obrovac et al. |
| 6,699,336 | B2 | 3/2004 | Turner et al. |
| 6,964,828 | B2 | 11/2005 | Lu et al. |
| 7,078,128 | B2 | 7/2006 | Lu et al. |
| 7,211,237 | B2 | 5/2007 | Eberman et al. |
| 7,438,993 | B2 * | 10/2008 | Shin et al. ............... 429/327 |
| 7,482,099 | B2 * | 1/2009 | Shin et al. ............... 429/326 |
| 7,482,100 | B2 * | 1/2009 | Shin et al. ............... 429/326 |
| 7,491,470 | B2 * | 2/2009 | Shin et al. ............... 429/326 |
| 7,507,503 | B2 | 3/2009 | Amine et al. |
| 7,851,092 | B2 * | 12/2010 | Amine et al. ........... 429/326 |
| 7,968,235 | B2 | 6/2011 | Amine et al. |
| 8,481,216 | B2 * | 7/2013 | Ahn et al. ............... 429/330 |
| 8,609,287 | B2 * | 12/2013 | Zhang et al. ........... 429/336 |
| 2003/0027048 | A1 | 2/2003 | Lu et al. |
| 2003/0211390 | A1 | 11/2003 | Dahn et al. |
| 2004/0121234 | A1 | 6/2004 | Le |
| 2004/0121239 | A1 | 6/2004 | Abe et al. |
| 2004/0131936 | A1 | 7/2004 | Turner et al. |
| 2004/0179993 | A1 | 9/2004 | Dahn et al. |
| 2005/0019670 | A1 | 1/2005 | Amine et al. |
| 2005/0031957 | A1 | 2/2005 | Christensen et al. |
| 2005/0221196 | A1 | 10/2005 | Dahn et al. |
| 2006/0045144 | A1 | 3/2006 | Karlsen et al. |
| 2006/0046144 | A1 | 3/2006 | Obrovac |
| 2006/0199080 | A1 * | 9/2006 | Amine et al. ........... 429/326 |
| 2006/0263695 | A1 | 11/2006 | Dahn et al. |
| 2007/0072085 | A1 | 3/2007 | Chen et al. |
| 2009/0286162 | A1 | 11/2009 | Lamanna et al. |

FOREIGN PATENT DOCUMENTS

| | | |
|---|---|---|
| JP | 06-338347 | 12/1994 |
| JP | 07-302614 | 11/1995 |
| JP | 2000-058117 | 2/2000 |
| JP | 2002-260730 | 9/2002 |
| JP | 2004-063112 | 2/2004 |
| JP | 2004-234948 | 8/2004 |

| | | |
|---|---|---|
| JP | 2004-349132 | 12/2004 |
| WO | WO-01/29920 | 4/2001 |

OTHER PUBLICATIONS

Chen, J. et al., "Chemical Overcharge and Overdischarge Protection for Lithium-Ion Batteries," Electrochemical and Solid-State Letters, 8 (1), pp. A59-A62, (2005), published by the Electrochemical Society, Inc.
Chen, Z. et al., "Bifunctional Electrolyte Additive for Lithium-Ion Batteries", Electrochemistry Communications, 9, (2007), pp. 703-707.
Chen, Z. et al., "Redox Shuttles for Safer Lithium-Ion Batteries", Electrochimica Acta 54 (2009) pp. 5605-5613.
Chen, Z. et al., "Understanding the Stability of Aromatic Redox Shuttles for Overcharge Protection of Lithium-Ion Cells," Journal of Electrochemical Society, 153, 2006, A2215-A2219.
Moshurchak, L.M. et al., "High-Potential Redox Shuttle for Use in Lithium-Ion Batteries", Journal of the Electrochemical Society, 156, (4), (2009), pp. A309-A312.

* cited by examiner

*Primary Examiner* — Patrick Ryan
*Assistant Examiner* — Lucas J O Donnell
(74) *Attorney, Agent, or Firm* — Foley & Lardner LLP

(57) ABSTRACT

A compound has general Formula I, II, III, or IV:

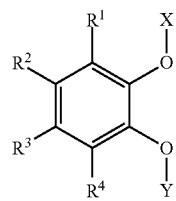

I

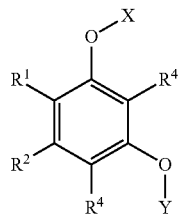

II

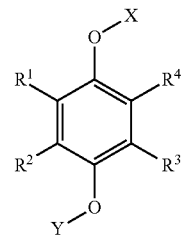

III

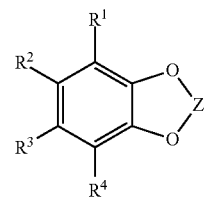

IV where X and Y are independently a group of Formula (A):

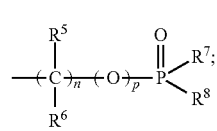

(A)

and
Z a group of Formula (B):

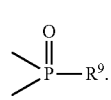

(B)

The compounds may be used in electrolytes and electrochemical devices.

18 Claims, 6 Drawing Sheets

REDOX SHUTTLES FOR HIGH VOLTAGE CATHODES

CROSS-REFERENCE TO RELATED APPLICATIONS

This application claims the benefit of U.S. Provisional Patent Application No. 61/348,050, filed on May 25, 2010, the entire disclosure of which is incorporated herein by reference for any and all purposes.

GOVERNMENT INTERESTS

The United States Government has rights in this invention pursuant to Contract No. DE-AC02-06CH11357 between the United States Government and UChicago Argonne, LLC, representing Argonne National Laboratory.

FIELD

The present invention relates in general to the field of lithium rechargeable batteries, and more particularly relates to the use of reduction oxidation (e.g. redox) shuttles in electrochemical cells and batteries.

BACKGROUND

Lithium ion batteries were first commercialized in 1990, and soon thereafter drew tremendous attention from academic and industry interests due to the advantages such as high energy density and rapid charge/discharge capabilities in comparison to state of the battery technology at the time. In recent years, lithium ion battery technology has become the most popular power source for portable electronic devices. In addition, lithium ion batteries have found application in hybrid electric vehicles (HEV) and plug-in hybrid electric vehicles (PHEV). However, safety of lithium batteries continues to plague the technology. For example, secondary lithium-ion batteries are known to exhibit problems in shorting of the battery, elevated operating temperatures and overcharge, which can lead to dangerous situations such as overheating, fire, and explosion of the battery.

Overcharge occurs when electricity flow is forced through a cell when its capacity is already full. This is one of the most common factors that could lead to serious safety issues of lithium-ion batteries. Due to the manufacture processes, there is always a "weakest cell" in a battery pack (i.e. the cell with the lowest charging capability in a multi-cell battery pack). During charging, the weakest cell will reach full capacity prior to the other cells, but because the overall voltage of the battery is not high, the full capacity cell with not trigger the voltage monitor of the charger to read "full." As a result, the weakest cell is put into an overcharge situation. Instead of being stored evenly across all electrodes in the battery pack, electricity will build up in, and increase the potential of, the cathode in the weakest cell, causing the potential to go beyond the electrochemical window of the electrolyte. In turn, this will cause reactions to occur such as oxidation of the electrolyte, leading up to and including explosion of the cell and battery pack.

Known methods to avoid the overcharge abuse in practice, include the use of electronic devices attached to each individual cell to monitor for overcharge, the use of overcharge protection additives in each cell, and the use of redox shuttles in the electrolyte of the electrochemical cells.

A number of redox shuttle additives are known. Generally, the redox shuttle molecule can be reversibly oxidized and reduced at a defined potential slightly higher than the end-of-charge potential of the positive electrode. This mechanism can protect the cell from overcharge by locking the potential of the positive electrode at the oxidation potential of the shuttle molecules.

For an ideal redox shuttle compound, there are at least three desirable properties. The first property is that it should have a reversible oxidation potential that is appropriate for the cathode material with which it is to be used. This means that the oxidation potential of the redox shuttle should be between 0.3V and 0.5V volts higher than the end-of-charge potential of the cathode. This will ensure that redox shuttle is accessed only overcharge potentials. The second property is that the redox shuttle should be electrochemically stabile or reversible. The stability and reversibility of the redox shuttle will determine how much overcharge protection is provided. The third property is that the redox shuttle is to have sufficient solubility in the electrolyte system in order to have an effective amount of the redox shuttle available.

SUMMARY

In one aspect, a compound of Formula I, II, III, or IV is provided:

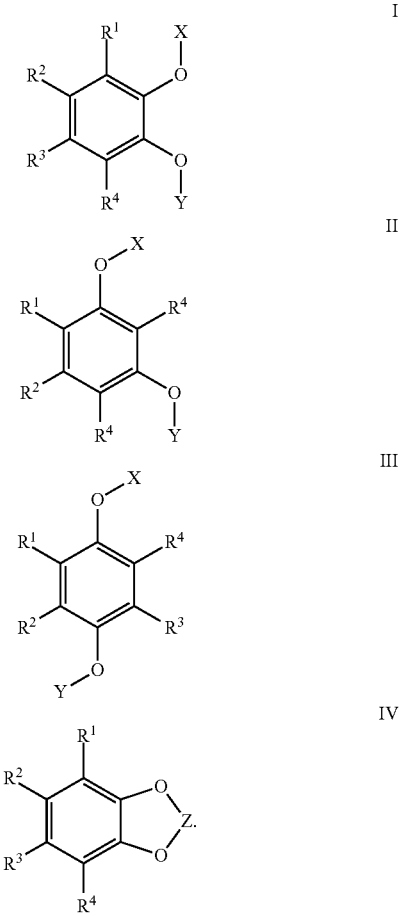

In such compounds, $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^2$ and $R^3$, or $R^3$ and $R^4$ join together to form a fused ring on the benzene ring; X and Y are independently a group of Formula (A):

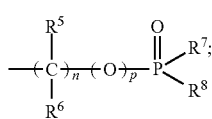

Z a group of Formula (B):

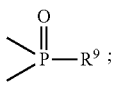

where $R^5$ and $R^6$ are independently H, F, Cl, Br, CN, $NO_2$, alkyl, a haloalkyl, phosphate, or polyether; $R^7$ and $R^8$ are independently H, F, Cl, Br, CN, $NO_2$, alkyl, alkoxy, haloalkyl, haloalkoxy, aryl, aryloxy, haloaryl, haloaryloxy, or polyether; $R^9$ is H, F, Cl, Br, CN, $NO_2$, alkyl, alkoxy, haloalkyl, haloalkoxy, aryl, aryloxy, haloaryl, haloaryloxy, or polyether; n is an integer from 0 to 8; and p is 0 or 1. In some embodiments, the compound is subject to the proviso that where n is 0, p is 0, and where n is from 1 to 8, p is 0 or 1.

In another aspect, an electrolyte is provided that includes a redox shuttle is an aromatic compound comprising at least one aromatic ring and at least one organophosphorus groups bonded to the aromatic ring through an oxygen atom. In various embodiments, the electrolyte also includes an alkali metal salt and a polar aprotic solvent. In some embodiments, the redox shuttle is a compound of Formula I, II, III, or IV as described above. Such electrolytes are substantially non-aqueous.

In another aspect, an electrochemical device is provided including a cathode, an anode; and any of the electrolytes described herein. In some embodiments, the electrochemical device is a lithium secondary battery; the cathode is a lithium metal oxide cathode; the anode is a carbon or lithium metal anode; and the anode and cathode are separated from each other by a porous separator.

In another aspect, a method of preparing the electrolytes described herein is provided. In some embodiments, the method includes combining an alkali metal salt and redox shuttle in a polar aprotic solvent; where the redox shuttle is an aromatic compound including at least one aromatic ring and at least one organophosphorus groups bonded to the aromatic ring through an oxygen atom. In other embodiments, the redox shuttle is a compound of Formula I, II, III, or IV.

DETAILED DESCRIPTION

Figure 1:
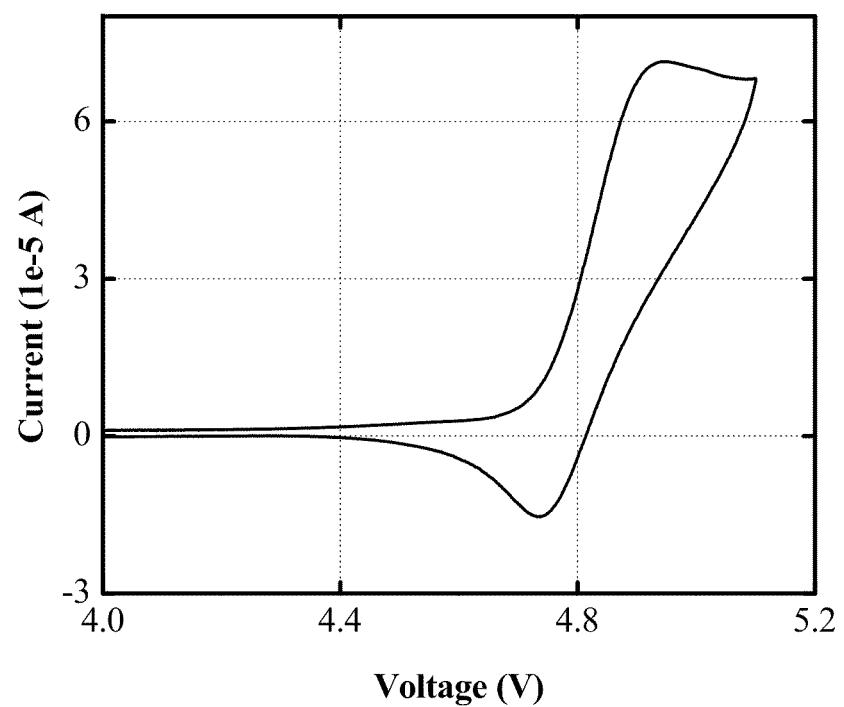
FIG. 1 is a cyclic voltammogram of 10 mM tetraethyl 2,5-di-tert-butyl-1,4-phenylene diphosphate in an electrolyte of 1.2 M $LiPF_6$ in EC/DEC (3:7 by weight) using a three electrode system (Pt working Electrode, Li counter electrode and Li reference electrode), according to Example 2.

In one aspect, provided is a compound of Formula I, II, III, or IV:

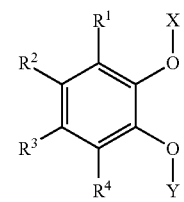

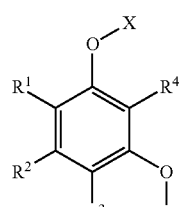

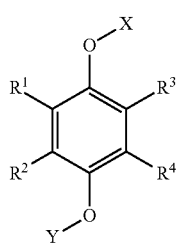

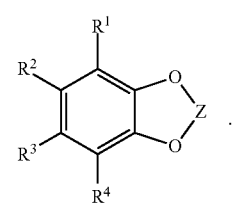

In the compounds of Formulas I, II, III, or IV, $R^1$, $R^2$, $R^3$, and $R^4$ are independently H, F, Cl, Br, CN, $NO_2$, a alkyl group, a haloalkyl group, a phosphate group, a polyether group; or $R^1$ and $R^2$, or $R^2$ and $R^3$, or $R^3$ and $R^4$, may join together to form a fused ring on the benzene ring; X and Y are independently a group of Formula A:

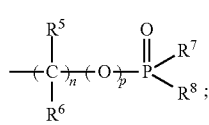

Z a group of Formula B:

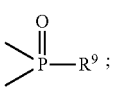

$R^5$ and $R^6$ are independently H, F, Cl, Br, CN, $NO_2$, a alkyl group, a haloalkyl group, a phosphate group, or a polyether group; $R^7$ and $R^8$ are independently H, F, Cl, Br, CN, $NO_2$, alkyl, alkoxy, haloalkyl, haloalkoxy, phenyl, phenoxy, halo, halogenated phenoxy, poly ether groups; $R^9$ is H, F, Cl, Br, CN, $NO_2$, a alkyl group, a alkoxy group, a haloalkyl group, haloaryl group, a phosphate group, or a polyether group; n is an integer from 0 to 8; p is 0 or 1; with the proviso that where n is 0, p is 0, and where n is from 1 to 8, p is 0 or 1. The compounds of Formulas I, II, III, and IV are also subject to the proviso that at least one of $R^1$, $R^2$, $R^3$, and $R^4$ is H or an alkyl group. In some embodiments, the proviso is that at least one of $R^1$, $R^2$, $R^3$, and $R^4$ is a tertiary alkyl group, and preferably at least two of $R^1$, $R^2$, $R^3$, and $R^4$ are tertiary alkyl groups. In some such embodiment, the tertiary alkyl groups have from 4 to 20 carbon atoms. Where $R^1$ and $R^2$, or $R^2$ and $R^3$, or $R^3$ and $R^4$, join together to form a fused ring on the benzene ring, two or more rings may be formed. For example, where these groups join to form a ring, the benzene ring may then be part of a larger ring system such as a naphthyl group, an anthracene group, a fluorenyl group, and the like. The compounds of Formula I, II, III, and IV may also be in the form of a salt.

In some embodiments, $R^1$, $R^2$, $R^3$, and $R^4$ are independently H, F, Cl, Br, I, a alkyl group, a haloalkyl group, or a polyether group. In some embodiments, $R^1$, $R^2$, $R^3$, and $R^4$ are independently H, F, Cl, Br, I, a $C_1$-$C_4$ alkyl group. In some embodiments, $R^1$ and $R^4$ are the same and are different from that of $R^2$ and $R^3$. In some embodiments, $R^1$ and $R^3$ are the same and are different from that of $R^2$ and $R^4$. In some embodiments, $R^1$ and $R^4$ are individually an alkyl group or a haloalkyl group, and $R^2$ and $R^3$ are H or F. In some embodiments, $R^1$ and $R^4$ are individually methyl, ethyl, n-propyl, iso-propyl, n-butyl, sec-butyl, or tert-butyl. In some embodiments, $R^1$ and $R^3$ are individually an alkyl group or a haloalkyl group, and $R^2$ and $R^4$ are H or F. In some embodiments, $R^1$ and $R^3$ are individually methyl, ethyl, n-propyl, iso-propyl, n-butyl, sec-butyl, or tert-butyl. In some embodiments, at least two of $R^1$, $R^2$, $R^3$, and $R^4$ are tert-butyl groups.

In some embodiments, the compound of Formula I, II, III, or IV is:

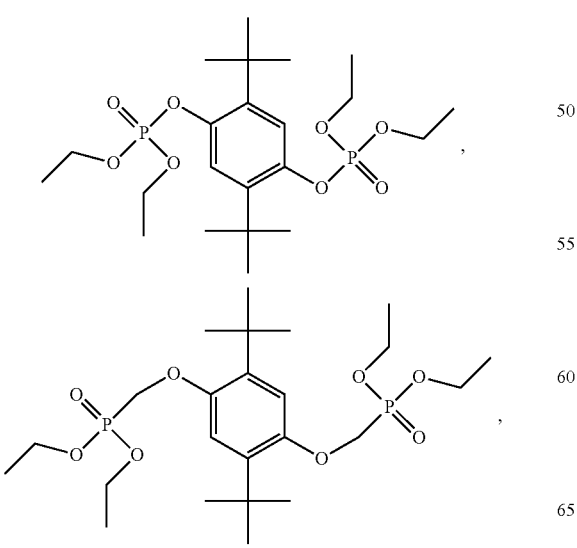

-continued

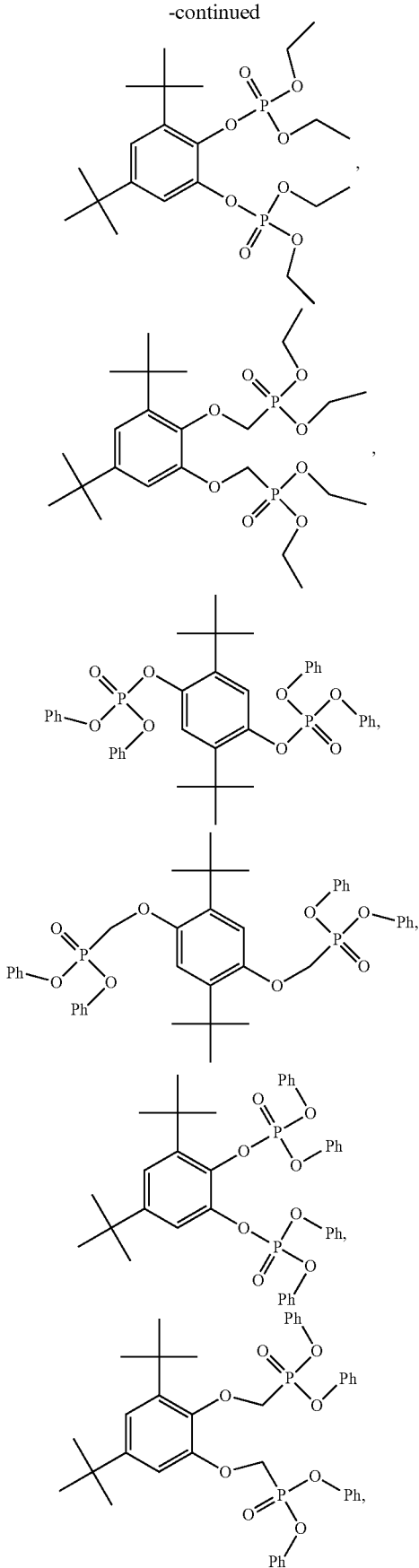

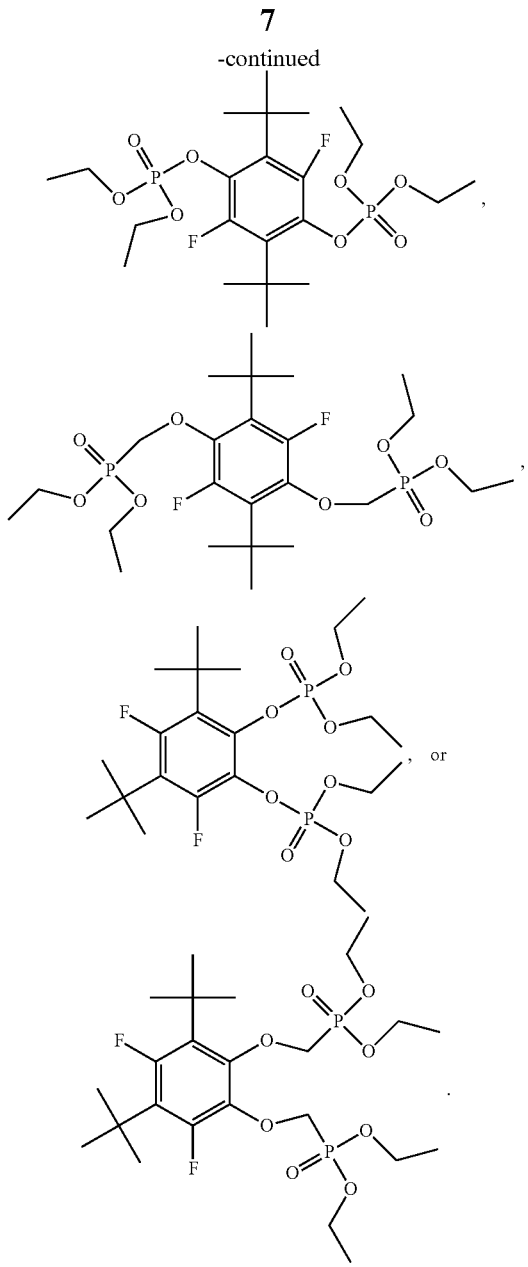

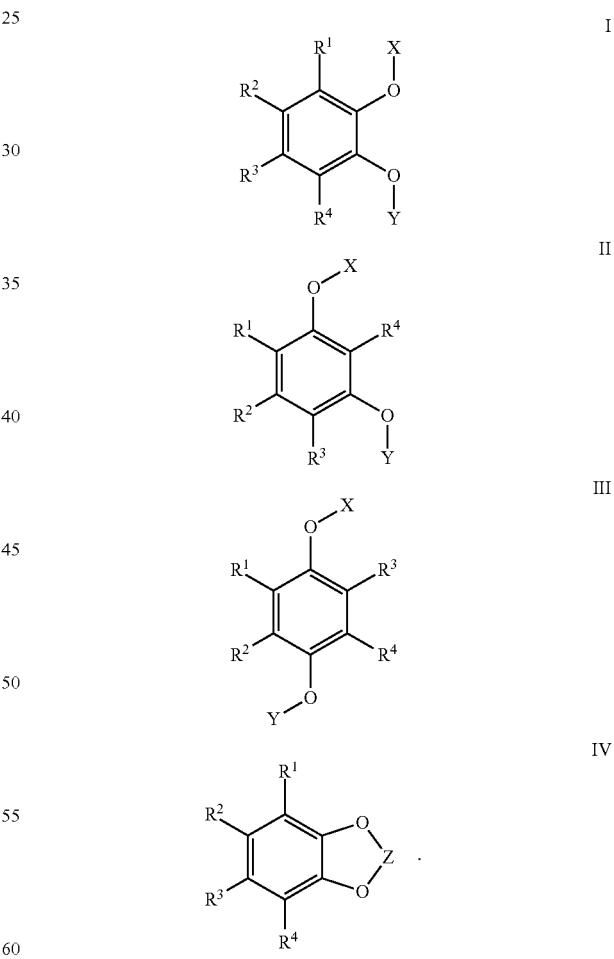

In another aspect, an electrolyte is provided that includes a redox shuttle, an alkali metal salt, and a polar aprotic solvent. In such embodiments, the redox shuttle is an aromatic compound having at least one aromatic ring having at least one organophosphorus groups bonded to the aromatic ring through an oxygen atom. In some embodiments, the redox shuttle has two or more organ phosphorus groups bonded to the aromatic ring through oxygen atoms. In some embodiments, the redox shuttle has two, three or four oxygen atoms. In all such embodiments, the electrolyte is preferably, substantially non-aqueous. As used herein, the term "substantially non-aqueous" refers to electrolytes having minimal or no water present. In some embodiments, there is less than 20 ppm water present in the electrolyte. In some embodiments, the redox shuttle has a redox potential of 3.5 to 5 V in the electrolyte. In other embodiments, the redox shuttle has a redox potential of 4.4 to 5 V in the electrolyte.

A variety of redox shuttles may be employed in lithium-ion batteries of the invention. Suitable redox shuttles have an electrochemical potential above (e.g., slightly above) the positive electrode's maximum normal operating potential. Thus, shuttle selection may be guided in part by positive electrode selection. As a general numeric guide, the shuttle may have a redox potential from 0.3 to 0.6 V above the positive electrode's maximum normal operating potential. For example, this may be from 3.7 V to 4.7 V vs. Li/Li$^+$, in some embodiments. In other embodiments, the redox potential of the shuttle is from 3.7 V to 4.4 V vs. Li/Li$^+$. In other embodiments, the redox potential of the shuttle is from 3.7 V to 4.2 V vs. Li/Li$^+$. In other embodiments, the redox potential of the shuttle is from 3.7 to 4.0 V vs. Li/Li$^+$. For example, LiFePO$_4$ positive electrodes have a recharge plateau of about 3.45 V vs. Li/Li$^+$, and exemplary shuttles for use with such electrodes may have a redox potential from 3.75 to 4.05 V vs. Li/Li$^+$. Similarly, LiMnPO$_4$ and LiMn$_2$O$_4$ electrodes have a recharge plateau of about 4.1V vs. Li/Li$^+$, and exemplary shuttles for use with such electrodes may have a redox potential from 4.4 V to 4.7 V vs. Li/Li$^+$.

In some embodiments, the redox shuttle is any of the compounds described above having general Formula I, II, III, or IV. In such embodiments, suitable redox shuttles are a compound of Formula I, II, III, or IV:

In the redox shuttles of Formulas I, II, III, or IV, $R^1$, $R^2$, $R^3$, and $R^4$ are independently H, F, Cl, Br, CN, NO$_2$, a alkyl group, a haloalkyl group, a phosphate group, a polyether group; or $R^1$ and $R^2$, or $R^2$ and $R^3$, or $R^3$ and $R^4$, may join together to form a fused ring on the benzene ring; X and Y are independently a group of Formula A:

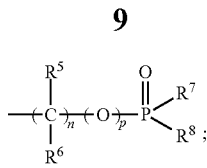

(A)

Z a group of Formula B:

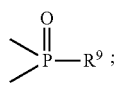

(B)

$R^5$ and $R^6$ are independently H, F, Cl, Br, CN, $NO_2$, a alkyl group, a haloalkyl group, a phosphate group, or a polyether group; $R^7$ and $R^8$ are independently H, F, Cl, Br, CN, $NO_2$, alkyl, alkoxy, haloalkyl, haloalkoxy, phenyl, phenoxy, halo, halogenated phenoxy, poly ether groups; $R^9$ is H, F, Cl, Br, CN, $NO_2$, a alkyl group, a alkoxy group, a haloalkyl group, haloaryl group, a phosphate group, or a polyether group; n is an integer from 0 to 8; p is 0 or 1; with the proviso that where n is 0, p is 0, and where n is from 1 to 8, p is 0 or 1. The redox shuttles of Formulas I, II, III, and IV are also subject to the proviso that at least one of $R^1$, $R^2$, $R^3$, and $R^4$ is H or an alkyl group. In some embodiments, the proviso is that at least one of $R^1$, $R^2$, $R^3$, and $R^4$ is a tertiary alkyl group, and preferably at least two of $R^1$, $R^2$, $R^3$, and $R^4$ are tertiary alkyl groups. In some such embodiments, the tertiary alkyl groups have from 4 to 20 carbon atoms. Where $R^1$ and $R^2$, or $R^2$ and $R^3$, or $R^3$ and $R^4$, join together to form a fused ring on the benzene ring, two or more rings may be formed. For example, where these groups join to form a ring, the benzene ring may then be part of a larger ring system such as a naphthyl group, an anthracene group, a fluorenyl group, and the like. The compounds of Formula I, II, III, and IV may also be in the form of a salt.

In some embodiments, $R^1$, $R^2$, $R^3$, and $R^4$ are independently H, F, Cl, Br, I, a alkyl group, a haloalkyl group, or a polyether group. In some embodiments, $R^1$, $R^2$, $R^3$, and $R^4$ are independently H, F, Cl, Br, I, a $C_1$-$C_4$ alkyl group. In some embodiments, $R^1$ and $R^4$ are the same and are different from that of $R^2$ and $R^3$. In some embodiments, $R^1$ and $R^3$ are the same and are different from that of $R^2$ and $R^4$. In some embodiments, $R^1$ and $R^4$ are individually an alkyl group or a haloalkyl group, and $R^2$ and $R^3$ are H or F. In some embodiments, $R^1$ and $R^4$ are individually methyl, ethyl, n-propyl, iso-propyl, n-butyl, sec-butyl, or tert-butyl. In some embodiments, $R^1$ and $R^3$ are individually an alkyl group or a haloalkyl group, and $R^2$ and $R^4$ are H or F. In some embodiments, $R^1$ and $R^3$ are individually methyl, ethyl, n-propyl, iso-propyl, n-butyl, sec-butyl, or tert-butyl. In some embodiments, at least two of $R^1$, $R^2$, $R^3$, and $R^4$ are tert-butyl groups.

In some embodiments, the redox shuttle of Formula I, II, III, or IV is:

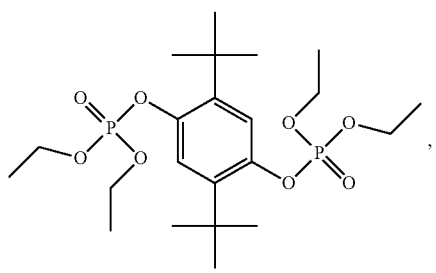

-continued

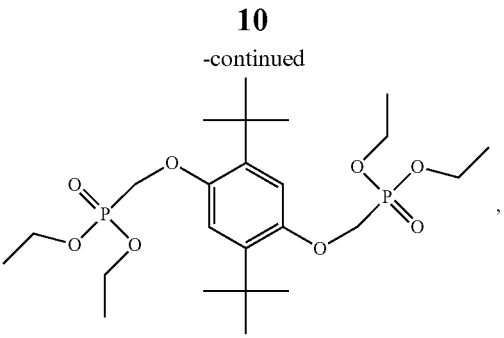

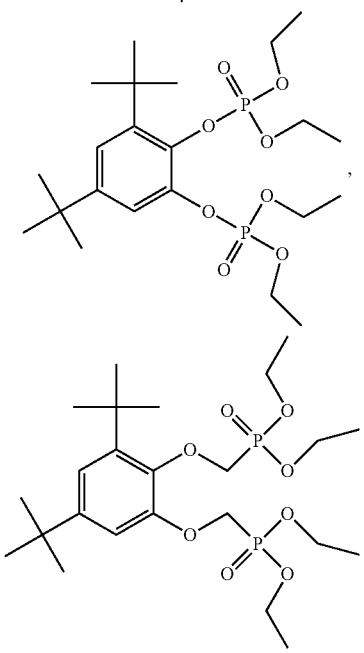

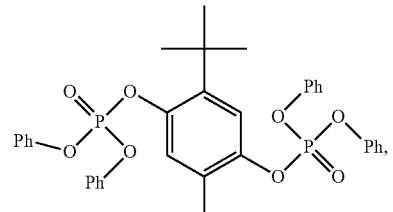

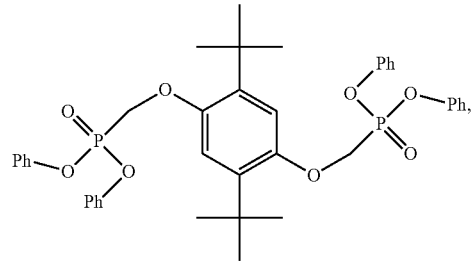

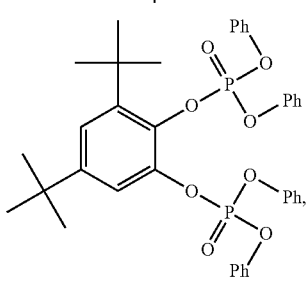

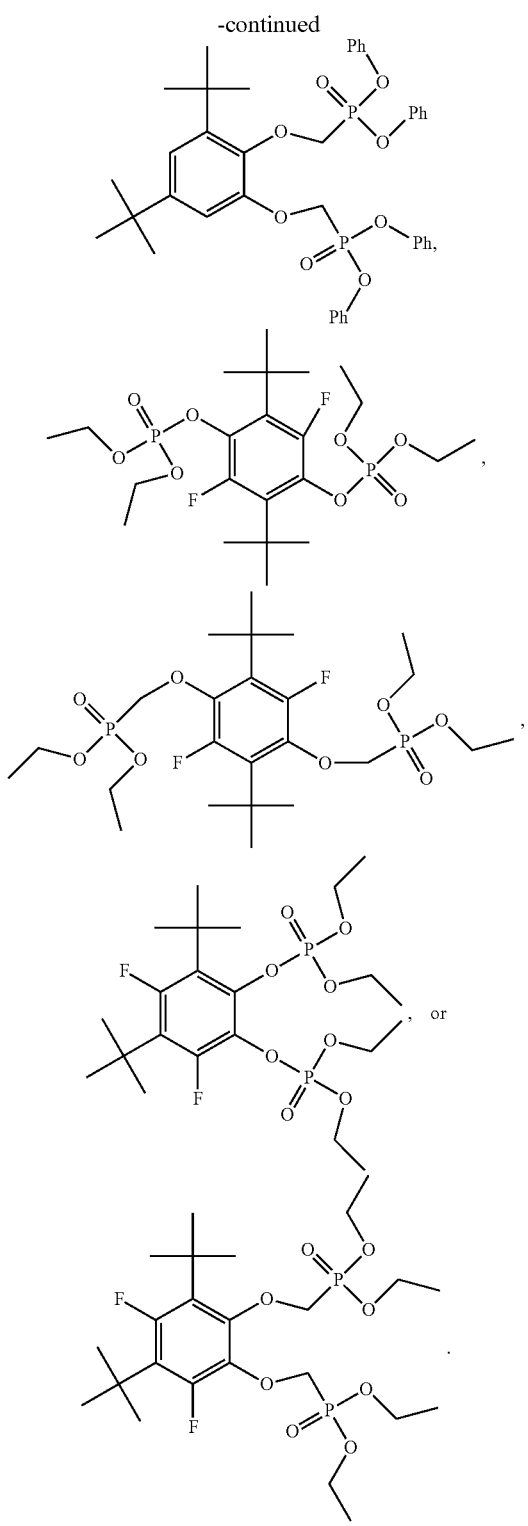

According to any of the described embodiments of the electrolyte, the concentration of the redox shuttle in the electrolyte ranges from 0.0005 wt % and 50 wt %. The preferred concentration is from 1 wt % to 10 wt %.

A variety of alkali metal salts may be employed in the electrolytes for assisting in charge transfer through the electrolyte. Exemplary alkali metal salts include, but are not limited to lithium salts that are stable and soluble in the chosen charge-carrying media, such as $Li[B(C_2O_4)_2]$; $Li[BF_2(C_2O_4)]$; $LiClO_4$; $LiBF_4$; $LiAsF_6$; $LiSbF_6$; LiBr, $LiPF_6$; $Li[CF_3SO_3]$; $Li[N(CF_3SO_2)_2]$; $Li[C(CF_3SO_2)_3]$; $Li[B(C_6F_5)_4]$; $Li[B(C_6H_5)_4]$; $Li[N(SO_2CF_3)_2]$; $Li[N(SO_2CF_2CF_3)_2]$; $LiN(SO_2C_2F_5)_2$; $Li[BF_3C_2F_5]$; and $Li[PF_3(CF_2CF_3)_3]$; and lithium alkyl fluorophosphates. In some embodiments, the alkali metal salt is a mixture of any two or more such alkali metal salts.

According to any of the described embodiments of the electrolyte, the polar aprotic solvent is a liquid or gel capable of solubilizing sufficient quantities of an alkali salt and a redox shuttle so that a suitable quantity of charge may be transported from the positive electrode to the negative electrode. Exemplary polar aprotic solvents can be used over a wide temperature range, e.g., from −30° C. to 70° C. without freezing or boiling, and are stable in the electrochemical window within which the cell electrodes and redox shuttles operate. Suitable solvents include ethylene carbonate, propylene carbonate, dimethyl carbonate; ethyl methyl carbonate; diethyl carbonate; methyl propyl carbonate; ethyl propyl carbonate; dipropyl carbonate; bis(trifluoroethyl)carbonate; bis(pentafluoropropyl)carbonate; trifluoroethyl methyl carbonate; pentafluoroethyl methyl carbonate; heptafluoropropyl methyl carbonate; perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol; dimethyl ether; polyethylene glycols; sulfones; and γ-butyrolactone.

The redox shuttles, as noted above, have suitable solubility in carbonate-based electrolyte solvents and gels. For example, the redox shuttles may be prepared in carbonate-based electrolytes, such as, 1.2M $LiPF_6$ in EC/EMC 3/7 (i.e. an mixture of 3 parts ethylene carbonate and 7 parts ethylmethylcarbonate), or 1.2M $LiPF_6$ in EC/DEC 5/5 (i.e. a 1:1 mixture of ethylene carbonate and diethylcarbonate). According to various embodiments, electrolytes may be prepared with a redox shuttle at a concentration of from 0.005 wt % to 50 wt %, or from 0.1 wt % to 30 wt %. In other embodiments, the electrolytes may be prepared with a redox shuttle at a concentration of from 2% to 10%.

In some embodiments, any of the electrolytes may also include an electrode stabilizing compound that can be reduced or polymerized on the surface of a negative electrode to form a passivation film on the surface of the negative electrode. In other embodiments, any of the electrolytes may also include an electrode stabilizing compound that can be reduced or polymerized on the surface of a positive electrode to form a passivation film on the surface of the positive electrode. In some embodiments, each electrode stabilizing compound is present in the electrolyte at a concentration of 0.001 wt % to 8 wt %.

In another aspect, an electrochemical device includes a cathode; an anode; and any of the electrolytes described above. In some embodiments, the electrochemical device is a lithium secondary battery; the cathode is a lithium metal oxide cathode; the anode is a carbon or lithium metal anode; and the anode and cathode are separated from each other by a porous separator. In some such embodiments, the cathode is a spinel, olivine, or carbon-coated olivine cathode; and the anode is a graphite or amorphous carbon.

A variety of negative electrodes may be employed in lithium-ion batteries. Representative negative electrodes include $Li_4Ti_5O_{12}$; the lithium alloy compositions described in U.S. Pat. Nos. 6,203,944; 6,255,017; 6,436,578; 6,664,004; and 6,699,336; U.S. Patent Application Publication Nos. 2003/0211390; 2004/013 1936; 2005/0031957; and 2006/

046144; graphitic carbons e.g., those having a spacing between (002) crystallographic planes, $d_{002}$, of 3.45 Å>$d_{002}$>3.354 Å and existing in forms such as powders, flakes, fibers or spheres (e.g., mesocarbon microbeads (MCMB)); other materials that will be familiar to those skilled in the art; and combinations thereof.

A variety of positive electrodes may be employed in lithium-ion batteries of the invention. Representative cathode materials include, spinel; olivine; carbon-coated olivine; $LiFePO_4$; $LiCoO_2$; $LiNiO_2$; $LiNi_{1-x}CO_yMet_zO_2$; $LiMn_{0.5}Ni_{0.5}O_2$; $LiMn_{0.3}Co_{0.3}Ni_{0.3}O_2$; $LiMn_2O_4$; $LiFeO_2$; $LiMet_{0.5}Mn_{1.5}O_4$; $Li_{1+x}Ni_\alpha Mn_\beta Co_\gamma Met'_\delta O_{2-z'}F_{z'}$; $A_nB_2(XO_4)_3$ (Nasicon); and vanadium oxide; where Met is Al, Mg, Ti, B, Ga, Si, Mn, or Co; Met' is Mg, Zn, Al, Ga, B, Zr, or Ti; A is Li, Ag, Cu, Na, Mn, Fe, Co, Ni, Cu, and Zn; B is Ti, V, Cr, Fe, and Zr; X is P, S, Si, W, Mo; 0≤x≤0.3, 0≤y≤0.5, 0≤z≤0.5, 0≤m≤0.5 and 0≤n≤0.5; 0≤x'≤0.4, 0≤α≤1, 0≤β≤1, 0≤γ≤1, 0≤δ≤0.4, and 0≤z'≤0.4; and 0≤n'≤3. In some embodiments, positive electrodes include $LiFePO_4$, $LiMnPO_4$, $LiMn_2O_4$, $LiCoPO_4$, and $LiCoO_2$; lithium transition metal oxides as disclosed in U.S. Pat. Nos. 5,858,324; 5,900,385; 6,143,268; 6,680,145; 6,964,828; 7,078,128; and 7,211,237; U.S. Patent Application Publication Nos. 2003/0027048; 2004/0121234; 2004/0179993; and 2006/045144. In some embodiments, the positive electrode is $LiMnPO_4$, $LiMn_2O_4$, $LiCoPO_4$, or $LiCoO_2$.

The negative or positive electrode may contain additives such as will be familiar to those skilled in the art, e.g., carbon black for negative electrodes, and carbon black, flake graphite and the like for positive electrodes.

The negative and positive electrode capacities may optionally be selected to provide an excess negative electrode capacity, which enables the shuttle to provide overcharge protection. From 10% to 20% excess negative electrode capacity is recommended. Lesser or greater excess negative electrode capacities may be employed if desired.

Anodes and cathodes of an electrochemical device are typically in contact with a current collector so that it may be effectively carry the current. The current collector may also be an adjacent material, such as the shell of a lithium-ion button cell. A variety of arrangements will work, so long as the negative and positive electrodes make suitable electrical contact with their associated current collectors. To prevent lithium capture during recharging, the negative electrode current collector has a lithium alloying potential below the negative electrode's minimum normal operating potential. Thus the negative electrode current collector selection will be guided in part by the negative electrode selection. To discourage or prevent current collector dissolution during an over-discharge event, it may be helpful to employ a negative electrode current collector having a dissolution potential above the redox shuttle reduction potential. Thus the negative electrode current collector selection may also be guided in part by the redox shuttle selection. Representative negative electrode current collectors include aluminum, copper, stainless steels (e.g., 300 series and 400 series stainless steels), titanium, tantalum, niobium, and INCONEL™ nickel chromium alloys.

When the negative electrode has a larger irreversible first cycle capacity loss than that of the positive electrode, the positive electrode will normally remain at an elevated potential during an over-discharge event. The positive electrode current collector will be held near the same elevated potential and will not be susceptible to lithium capture during recharging or dissolution during over-discharging. Accordingly there are fewer constraints on selection of the positive electrode current collector. Representative positive electrode current collectors include, but are not limited to, aluminum, stainless steels (e.g., 300 series and 400 series stainless steels), titanium, tantalum, niobium, and INCONEL alloys.

In some aspects, the electrolytes may include other additives to enhance the performance of the electrolyte when used in an electrochemical cell. For example, the electrolytes may also include an electrode stabilizing additive to protect the electrodes from degradation. Such electrode stabilizing additives are described by co-pending U.S. patent application Ser. Nos. 10/857,365 and 11/279,120. Such electrode stabilizing additives can be reduced or polymerized on the surface of a negative electrode to form a passivation film on the surface of the negative electrode. Likewise, electrolytes can include an electrode stabilizing additive that can be oxidized or polymerized on the surface of the positive electrode to form a passivation film on the surface of the positive electrode. In some embodiments, the electrolytes further include mixtures of the two types of electrode stabilizing additives. The additives are typically present at a concentration of from 0.001 wt % to 8 wt %.

In some embodiments, the electrode stabilizing additive is a substituted or unsubstituted linear, branched or cyclic hydrocarbon including at least one oxygen atom and at least one aryl, alkenyl or alkynyl group. Passivating films may be formed from a substituted aryl compound or a substituted or unsubstituted heteroaryl compound where the additive includes at least one oxygen atom. Alternatively, a combination of two additives may be used. In some embodiments, one additive is selective for forming a passivating film on the cathode to prevent leaching of metal ions and the other additive can be selective for passivating the anode surface to prevent or lessen the reduction of metal ions at the anode. Representative electrode stabilizing additives include 1,2-divinyl furoate, 1,3-butadiene carbonate, 1-vinylazetidin-2-one, 1-vinylaziridin-2-one, 1-vinylpiperidin-2-one, 1 vinylpyrrolidin-2-one, 2,4-divinyl-1,3-dioxane, 2 amino-3 vinylcyclohexanone, 2-amino-3-vinylcyclopropanone, 2 amino-4-vinylcyclobutanone, 2-amino-5-vinylcyclopentanone, 2-aryloxy-cyclopropanone, 2-vinyl-[1,2]oxazetidine, 2 vinylaminocyclohexanol, 2-vinylaminocyclopropanone, 2 vinyloxetane, 2-vinyloxy-cyclopropanone, 3-(N-vinylamino)cyclohexanone, 3,5-divinyl furoate, 3-vinylazetidin-2-one, 3 vinylaziridin 2 one, 3 vinylcyclobutanone, 3 vinylcyclopentanone, 3 vinyloxaziridine, 3 vinyloxetane, 3-vinylpyrrolidin-2-one, 4,4 divinyl-3 dioxolan 2-one, 4 vinyltetrahydropyran, 5-vinylpiperidin-3-one, allylglycidyl ether, butadiene monoxide, butyl vinyl ether, dihydropyran-3-one, divinyl butyl carbonate, divinyl carbonate, divinyl crotonate, divinyl ether, divinyl ethylene carbonate, divinyl ethylene silicate, divinyl ethylene sulfate, divinyl ethylene sulfite, divinyl methoxypyrazine, divinyl methylphosphate, divinyl propylene carbonate, ethyl phosphate, methoxy-o-terphenyl, methyl phosphate, oxetan-2-yl-vinylamine, oxiranylvinylamine, vinyl carbonate, vinyl crotonate, vinyl cyclopentanone, vinyl ethyl-2-furoate, vinyl ethylene carbonate, vinyl ethylene silicate, vinyl ethylene sulfate, vinyl ethylene sulfite, vinyl methacrylate, vinyl phosphate, vinyl-2-furoate, vinylcylopropanone, vinylethylene oxide, β-vinyl-γ-butyrolactone, or a mixture of any two or more thereof. In some embodiments the electrode stabilizing additive may be a cyclotriphosphazene that is substituted with F, alkyloxy, alkenyloxy, aryloxy, methoxy, allyloxy groups, or combinations thereof. For example, the additive may be a (divinyl)-(methoxy)(trifluoro)cyclotriphosphazene, (trivinyl)(difluoro)(methoxy)cyclotriphosphazene, (vinyl)(methoxy)(tetrafluoro)cyclotriphosphazene, (aryloxy)(tetrafluoro)(methoxy)-cyclotriphosphazene, (diaryloxy)(trifluoro)

(methoxy)cyclotriphosphazene compounds, or a mixture of two or more such compounds. In some embodiments, the electrode stabilizing additive is vinyl ethylene carbonate, vinyl carbonate, or 1,2-diphenyl ether, or a mixture of any two or more such compounds.

Other representative electrode stabilizing additives may include compounds with phenyl, naphthyl, anthracenyl, pyrrolyl, oxazolyl, furanyl, indolyl, carbazolyl, imidazolyl, or thiophenyl groups. For example, electrode stabilizing additives may be aryloxpyrrole, aryloxy ethylene sulfate, aryloxy pyrazine, aryloxy-carbazole trivinylphosphate, aryloxy-ethyl-2-furoate, aryloxy-o-terphenyl, aryloxy-pyridazine, butyl-aryloxy-ether, divinyl diphenyl ether, (tetrahydrofuran-2-yl)-vinylamine, divinyl methoxybipyridine, methoxy-4-vinylbiphenyl, vinyl methoxy carbazole, vinyl methoxy piperidine, vinyl methoxypyrazine, vinyl methyl carbonate-allylanisole, vinyl pyridazine, 1-divinylimidazole, 3-vinyltetrahydrofuran, divinyl furan, divinyl methoxy furan, divinylpyrazine, vinyl methoxy imidazole, vinylmethoxy pyrrole, vinyltetrahydrofuran, 2,4-divinyl isooxazole, 3,4 divinyl-1-methylpyrrole, aryloxyoxetane, aryloxy-phenyl carbonate, aryloxy-piperidine, aryloxy-tetrahydrofuran, 2-aryl-cyclopropanone, 2-diaryloxy-furoate, 4-allylanisole, aryloxy-carbazole, aryloxy-2-furoate, aryloxy-crotonate, aryloxy-cyclobutane, aryloxy-cyclopentanone, aryloxy-cyclopropanone, aryloxy-cyclolophosphazene, aryloxy-ethylene silicate, aryloxy-ethylene sulfate, aryloxy-ethylene sulfite, aryloxy-imidazole, aryloxy-methacrylate, aryloxy-phosphate, aryloxy-pyrrole, aryloxyquinoline, diaryloxycyclotriphosphazene, diaryloxy ethylene carbonate, diaryloxy furan, diaryloxy methyl phosphate, diaryloxy-butyl carbonate, diaryloxy-crotonate, diaryloxy-diphenyl ether, diaryloxy-ethyl silicate, diaryloxy-ethylene silicate, diaryloxy-ethylene sulfate, diaryloxyethylene sulfite, diaryloxy-phenyl carbonate, diaryloxy-propylene carbonate, diphenyl carbonate, diphenyl diaryloxy silicate, diphenyl divinyl silicate, diphenyl ether, diphenyl silicate, divinyl methoxydiphenyl ether, divinyl phenyl carbonate, methoxycarbazole, or 2,4-dimethyl-6-hydroxy-pyrimidine, vinyl methoxyquinoline, pyridazine, vinyl pyridazine, quinoline, vinyl quinoline, pyridine, vinyl pyridine, indole, vinyl indole, triethanolamine, 1,3-dimethyl butadiene, butadiene, vinyl ethylene carbonate, vinyl carbonate, imidazole, vinyl imidazole, piperidine, vinyl piperidine, pyrimidine, vinyl pyrimidine, pyrazine, vinyl pyrazine, isoquinoline, vinyl isoquinoline, quinoxaline, vinyl quinoxaline, biphenyl, 1,2-diphenyl ether, 1,2-diphenylethane, o terphenyl, N-methylpyrrole, naphthalene, or a mixture of any two or more such compounds.

In other embodiments, electrode stabilizing additives include substituted or unsubstituted spirocyclic hydrocarbons containing at least one oxygen atom and at least one alkenyl or alkynyl group. For example, such stabilizing additives include those having Formula V:

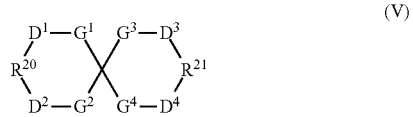

(V)

where: $D^1$, $D^2$, $D^3$, and $D^4$ are independently O or $CR^{22}R^{23}$; provided that $D^1$ is not O when $G^1$ is O, $D^2$ is not O when $G^2$ is O, $D^3$ is not O when $G^3$ is O, and $D^4$ is not O when $G^4$ is O; $G^1$, $G^2$, $G^3$, and $G^4$ are independently O or $CR^{22}R^{23}$; provided that $G^1$ is not O when $D^1$ is O, $G^2$ is not O when $D^2$ is O, $G^3$ is not O when $D^3$ is O, and $G^4$ is not O when $D^4$ is O; $R^{20}$ and $R^{21}$ are independently a substituted or unsubstituted divalent alkenyl or alkynyl group; $R^{22}$ and $R^{23}$ at each occurrence are independently H, F, Cl, a substituted or an unsubstituted alkyl, alkenyl, or alkynyl group.

Representative examples of Formula V include, but are not limited to, 3,9 divinyl-2,4,8,10-tetraoxaspiro[5.5]undecane, 3,9-divinyl-2,4,8-trioxaspiro[5.5]undecane, 3,9-divinyl-2,4-dioxaspiro[5.5]undecane, 3,9-diethylidene-2,4,8,10-tetraoxaspiro[5.5]undecane, 3,9-diethylidene-2,4,8-trioxaspiro[5.5]undecane, 3,9-diethylidene-2,4-dioxaspiro[5.5]undecane, 3,9-dimethylene-2,4,8,10-tetraoxaspiro[5.5]undecane, 3,9-divinyl-1,5,7,11-tetraoxaspiro[5.5]undecane, 3,9 dimethylene-1,5,7,11-tetraoxaspiro[5.5]undecane, 3,9 diethylidene-1,5,7,11-tetraoxaspiro[5.5]undecane, or a mixture of any two or more such compounds. Furthermore, mixtures of any two or more electrode stabilizing additives may also be used in the electrolytes.

In some embodiments, the electrode stabilizing additive is an anion receptor. In some embodiments, the anion receptor is a Lewis acid. In other embodiments, the anion receptor is a borane, a boronate, a borate, a borole, or a mixture of any two or more such compounds. In some embodiments, the anion receptor is a compound of the Formula VI:

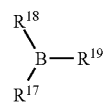

VI where, each $R^{17}$, $R^{18}$, and $R^{19}$ are independently halogen, alkyl, aryl, halogen-substituted alkyl, halogen-substituted aryl, or $OR^{17}$; or any two of $R^{17}$, $R^{18}$, and $R^{19}$, together with the atoms to which they are attached, form a heterocyclic ring having 5-9 members, and $R^{17}$ is at each occurrence independently alkyl, aryl, halogen-substituted alkyl, or halogen-substituted aryl.

In some embodiments, the anion receptors include, but not limited to, tri(propyl)borate, tris(1,1,1,3,3,3-hexafluoro-propan-2-yl)borate, tris(1,1,1,3,3,3-hexafluoro-2-phenyl-propan-2-yl)borate, tris(1,1,1,3,3,3-hexafluoro-2-(trifluoromethyl)propan-2-yl)borate, triphenyl borate, tris(4-fluorophenyl)borate, tris(2,4-difluorophenyl)borate, tris(2,3,5,6-tetrafluorophenyl)borate, tris(pentafluorophenyl)borate, tris(3-(trifluoromethyl)phenyl)borate, tris(3,5-bis(trifluoromethyl)phenyl)borate, tris(pentafluorophenyl)borane, or a mixture of any two or more thereof. Further suitable additives include 2-(2,4-difluorophenyl)-4-fluoro-1,3,2-benzodioxaborole, 2-(3-trifluoromethyl phenyl)-4-fluoro-1,3,2-benzodioxaborole, 2,5-bis(trifluoromethyl)phenyl-4-fluoro-1,3,2-benzodioxaborole, 2-(4-fluorophenyl)-tetrafluoro-1,3,2-benzodioxaborole, 2-(2,4-difluorophenyl)-tetrafluoro-1,3,2-benzodioxaborole, 2-(pentafluorophenyl)-tetrafluoro-1,3,2-benzodioxaborole, 2-(2-trifluoromethyl phenyl)-tetrafluoro-1,3,2-benzodioxaborole, 2,5-bis(trifluoromethyl phenyl)-tetrafluoro-1,3,2-benzodioxaborole, 2-phenyl-4,4,5,5-tetra(trifluoromethyl)-1,3,2-benzodioxaborolane, difluorophenyl-4,4,5,5-tetrakis(trifluoromethyl)-1,3,2-dioxaborolane, 2-(3,5-difluorophenyl-4,4,5,5-tetrakis(trifluoromethyl)-1,3,2-dioxaborolane, 2-pentafluorophenyl-4,4,5,5-tetrakis(trifluoromethyl)-1,3,2-dioxaborolane, bis(1,1,1,3,3,3-hexafluoroisopropyl)phenyl-boronate, bis(1,1,1,3,3,3-hexafluoroisopropyl)-3,5-difluorophenylboronate, bis(1,1,1,3,3,3-hexafluoroisopropyl)pentafluorophenylboronate, or a mixture of any two or more such compounds. In some embodiments, each anion receptor is present at a concentration from 0.001 wt % to 10 wt %.

In some other embodiments, the electrolyte includes as an electrolyte additive, $Li_2B_{12}X_{12-n}H_n$, $Li_2B_{10}X_{10-n'}H_{n'}$, or a mixture of two or more of such compounds. Such electrolyte additives may be present from 0.001 wt % to 15 wt %. In such compounds, X is OH, OCH$_3$, F, Cl, Br, or I, n is an integer from 0 to 12, and n' is an integer from 0 to 10.

In some embodiments, the electrolyte further includes a gel. Such electrolytes include a polar aprotic solvent; a lithium salt; a redox shuttle; a crosslinking agent; monofunctional monomeric compound; and at least one radical reaction initiator. In some embodiments, the gel electrolyte can also include other electrode stabilization additives and other electrolyte additives. Suitable crosslinking agents may be represented by Formula VII:

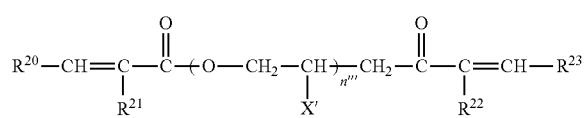

where $R^{20}$, $R^{21}$, $R^{22}$, and $R^{23}$ are each independently hydrogen, a substituted or unsubstituted alkyl group having from 1 to 12 carbon atoms, or a substituted or unsubstituted alkenyl group having from 2 to 12 carbon atoms; and where X' is a hydrogen, methyl, or ethyl group, and n''' is an integer from 1 to 15. Monofunctional monomeric compounds may be used for the control of the crosslinking density of the gel electrolyte. Suitable monofunctional monomeric compounds include those of Formula VIII:

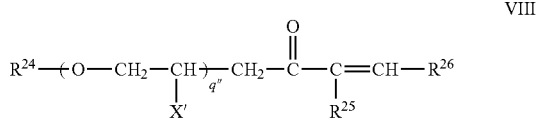

where $R^{24}$ is an alkyl group having from 1 to 12 carbon atoms; $R^{25}$ and $R^{26}$ are each independently a hydrogen, a substituted or unsubstituted alkyl group having from 1 to 12 carbon atoms, or a substituted or unsubstituted alkenyl group having from 2 to 12 carbon atoms; X' is hydrogen, methyl or ethyl group; and q'' is an integer from 1 to 20.

Crosslinking agents and monofunctional monomeric compounds provide a physical framework, or gel, after crosslinking to host the polar aprotic solvent. Variation of the amount of the crosslinking agent and monofunctional monomeric compound in the gel may impact the conductivity of the gel electrolyte, due to changes in viscosity. Lower viscosity gels are prepared with higher concentrations of monofunctional monomeric compound, as compared to the concentration of monofunctional monomeric compound used for higher viscosity gels. Without being bound by theory, higher viscosity gels may be expected to have lower electrochemical conductivity, while lower viscosity gels may be expected to have higher electrochemical conductivity. However, other electrochemical properties of the gel electrolyte, or an electrochemical cell prepared with the gel electrolyte, such as oxidation potential and reduction potential, are not expected to be impacted.

Polymerization of crosslinking agents and monofunctional monomeric compounds are known to those of skill in the art. For example, monofunctional monomeric compounds may be polymerized by thermal and photo initiation. Representative thermal initiators include, but are not limited to, an azo compound, a peroxide compound, bismaleimide, or a mixture of any two or more thereof. One example of an azo compound is azoisobutyronitrile. One example of a peroxide compound is benzoylperoxide. Representative photoinitiators include, but are not limited to, 1-hydroxyl-phenyl-ketone, benzophenone, 2-hydroxyl-2-methyl-1-phenyl-propanone, 2-hydroxyl-1-[4-(2-hydroxy)phenyl]-2-methyl-1-propanone, methylbenzoylformate, oxy-phenyl-acetic acid 2-[2-oxo-2-phenyl-acetoxy-ethoxy]-ethyl ester, oxy-phenyl-acetic 2-[2-hydroxy-ethoxy]-ethyl ester, α,α-dimethoxy-α-phenylacetophenone, 2-benzyl-2-(dimethylamino)-1-[4-(4-morpholinyl)phenyl]-1-propanone, diphenyl(2,4,6-trimethylthio)phenyl)-phosphine oxide, phosphine oxide, phenyl bis(2,4,6-trimethyl benzoyl), bis($\eta^5$-2,4-cyclopentadien-1-yl)bis[2,6-difluoro-3-(1H-pyrrol-1-yl)phenyl]titanium, iodonium (4-methylphenyl)-[4-(2-methylpropyl)phenyl]-hexafluorophosphate, or a mixture of two or more thereof. In some instances the photoinitiator is a UV initiator.

In another aspect, method of preparing the above electrolytes include combining an alkali metal salt and a compound of Formula I, II, III, or IV in a polar aprotic solvent.

In another aspect, electrochemical devices including the above redox shuttles are provided. Such electrochemical devices include, but are not limited to lithium ion batteries, supercapacitors, lithium batteries, lithium air battery and sodium batteries.

The following terms are used throughout as defined below.

The term "spinel" refers to manganese-based spinel such as, e.g., $Li_{1+x}Mn_{2-z}Met_yO_{4-m}X_n$, wherein Met is Al, Mg, Ti, B, Ga, Si, Ni, or Co; X is S or F; and wherein $0 \leq x \leq 0.3$, $0 \leq y \leq 0.5$, $0 \leq z \leq 0.5$, $0 \leq m \leq 0.5$ and $0 \leq n \leq 0.5$.

The term "olivine" refers to iron-based olivine such as, e.g., $LiFe_{1-z}Met''_yPO_{4-m}X_n$, wherein Met'' is Al, Mg, Ti, B, Ga, Si, Ni, Mn or Co; X is S or F; and wherein 0.3; $0 \leq y \leq 0.5$, $0 \leq z \leq 0.5$, $0 \leq m \leq 0.5$ and $0 \leq n \leq 0.5$.

Alkyl groups include straight chain and branched alkyl groups having from 1 to about 20 carbon atoms, and typically from 1 to 12 carbons or, in some embodiments, from 1 to 8 carbon atoms. As employed herein, "alkyl groups" include cycloalkyl groups as defined below. Examples of straight chain alkyl groups include methyl, ethyl, n-propyl, n-butyl, n-pentyl, n-hexyl, n-heptyl, and n-octyl groups. Examples of branched alkyl groups include, but are not limited to, isopropyl, sec-butyl, t-butyl, neopentyl, and isopentyl groups. Representative substituted alkyl groups may be substituted one or more times with, for example, amino, thio, hydroxy, cyano, alkoxy, and/or halo groups such as F, Cl, Br, and I groups.

Cycloalkyl groups are cyclic alkyl groups such as, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 6, or 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups may be mono-substituted or substituted more than once, such as, but not limited to: 2,2-; 2,3-; 2,4-; 2,5-; or 2,6-disubstituted cyclohexyl groups or mono-, di-, or tri-substituted norbornyl or cycloheptyl groups, which may be substituted with, for example, alkyl, alkoxy, amino, thio, hydroxy, cyano, and/or halo groups.

Alkenyl groups are straight chain, branched or cyclic alkyl groups having 2 to about 20 carbon atoms, and further including at least one double bond. In some embodiments alkenyl groups have from 1 to 12 carbons, or, typically, from 1 to 8 carbon atoms. Alkenyl groups include, for instance, vinyl, propenyl, 2-butenyl, 3-butenyl, isobutenyl, cyclohexenyl, cyclopentenyl, cyclohexadienyl, butadienyl, pentadienyl, and hexadienyl groups among others. Alkenyl groups may be substituted similarly to alkyl groups. Divalent alkenyl groups, i.e., alkenyl groups with two points of attachment, include, but are not limited to, CH—CH=CH$_2$, C=CH$_2$, or C=CHCH$_3$.

Alkynyl groups are straight chain or branched alkyl groups having 2 to about 20 carbon atoms, and further including at least one triple bond. In some embodiments alkynyl groups have from 1 to 12 carbons, or, typically, from 1 to 8 carbon atoms. Exemplary alkynyl groups include, but are not limited to, ethynyl, propynyl, and butynyl groups. Alkynyl groups may be substituted similarly to alkyl groups. Divalent alkynyl groups, i.e., alkynyl groups with two points of attachment, include but are not limited to CH—C≡CH.

One skilled in the art will readily realize that all ranges discussed can and do necessarily also describe all subranges therein for all purposes, and that all such subranges also form part and parcel of this invention. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

Example 1

Synthesis of tetraethyl-2,5-di-tert-butyl-1,4-phenylene diphosphate (TEDBPDP)

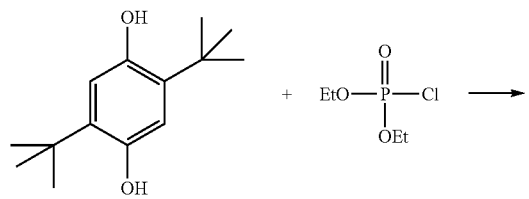

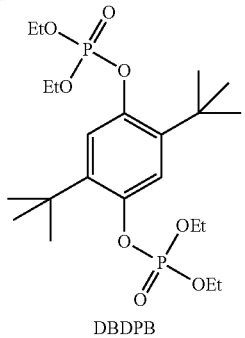

DBDPB 2,5-Di-tert-butylhydroquinone (9 mmol) was dissolved in anhydrous dichloromethane (DCM; 20 ml). Di-isopropy-ethylamine (DIPEA; 0.6 mmol) was added to the solution and the temperature was cooled down to −78° C. After cooling, diethyl-chloro-phosphonate (DECP, 3 ml, 22 mmol) was added dropwise and the reaction stirred overnight before tert-butylhydroperoxide (tBPO) was added. After stirring, the solvent was removed in vacuo, and the residue was partitioned between DCM and aqueous NaHCO$_3$ (0.1M). The organic portion was separated and dried over Na$_2$SO$_4$, before removing the solvent in vacuo. The crude product was crystallized from DCM to afford tetraethyl 2,5-di-tert-butyl-1,4-phenylene diphosphate (70% yield). $^1$H NMR (300 MHz, CDCl$_3$): δ/ppm 7.41 (s, 2H), 4.2 (t, 8H), 1.3 (d, 30H).

Example 2

Cyclic voltammograms of 10 mM tetraethyl 2,5-di-tert-butyl-1,4-phenylene diphosphate in an electrolyte of 1.2 M LiPF$_6$ in EC/DEC (3:7, by weight) were recorded. See FIG. 1. As shown, the oxidation begins at about 4.7 V vs. Li, and the oxidation current peaks at 5.0 V vs. Li. The reducing reaction is exhibited as a big hump during the reverse scan. The reduction current peaks at about 4.7 V vs. Li. In case of overcharging, the reduction reaction occurs at the negative electrodes, whose potential is always around 0 V vs. Li (<<4.7 V). Therefore, tetraethyl-2,5-di-tert-butyl-1,4-phenylene diphosphate is capable of protecting lithium-ion batteries from being overcharged.

Example 3

Figure 2:
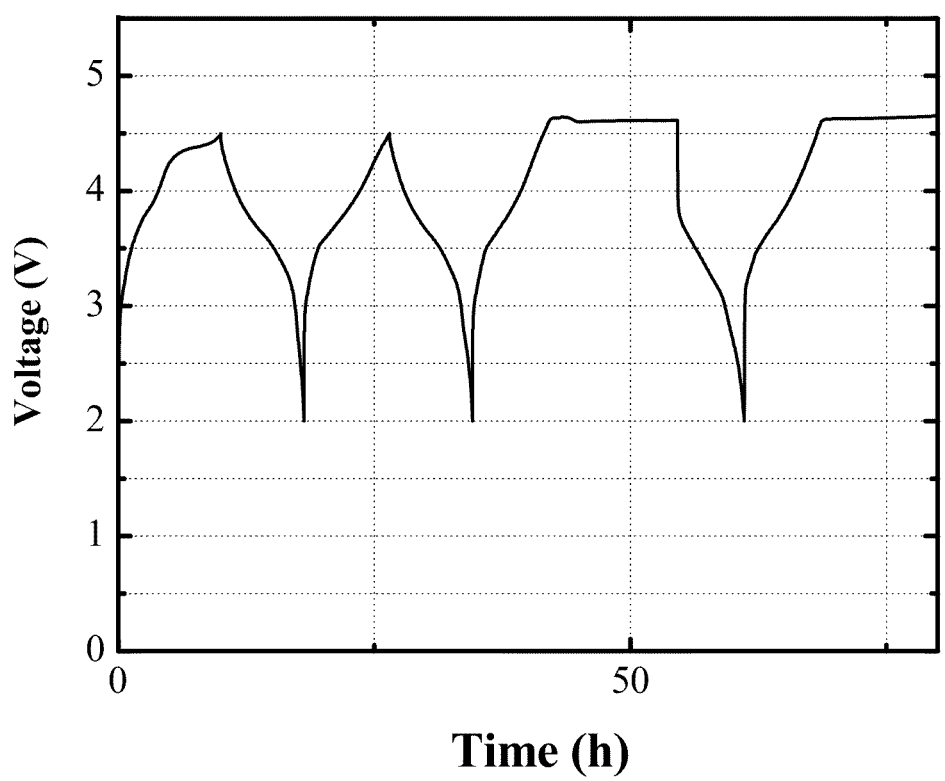
FIG. 2 is a graph of cell potential vs. time for a $Li_{1.2}Ni_{0.15}CO_{0.1}Mn_{0.55}O_2$/MCMB cell containing 5 wt % tetraethyl 2,5-di-tert-butyl-1,4-phenylene diphosphate, according to one embodiment.

Cell potential vs. time curves were recorded for Li$_{1.2}$Ni$_{0.15}$Co$_{0.1}$Mn$_{0.55}$O$_2$/MCMB cells containing 5 wt % of a redox shuttle of tetraethyl 2,5-di-tert-butyl-1,4-phenylene diphosphate in an electrolyte of 1.2 M LiPF$_6$ in EC/EMC (3:7 by weight), and at a charging rate of C/10. See FIG. 2. The first two cycles were formation process and the cut-off voltage was 4.6 V and 2.0 V. During the first 10 hours of testing, the normal charging plateau for the Li$_{1.2}$Ni$_{0.15}$CO$_{0.1}$Mn$_{0.55}$O$_2$/MCMB cell is observed at about 4 V. Starting from the third cycle, once the cells are fully charged, the potential rises rapidly to about 4.7 V, where the shuttle is activated and carries the current through the lithium-ion cells. Therefore, the cell voltage is nearly invariant under the help of the redox shuttle added otherwise the cell voltage would rise rapidly until triggering electrochemical reaction of the cell components. After the 20 hours charging period, the current was reversed and the cell was discharged to a cutoff voltage of 2.0 V.

Example 4

Figure 3:
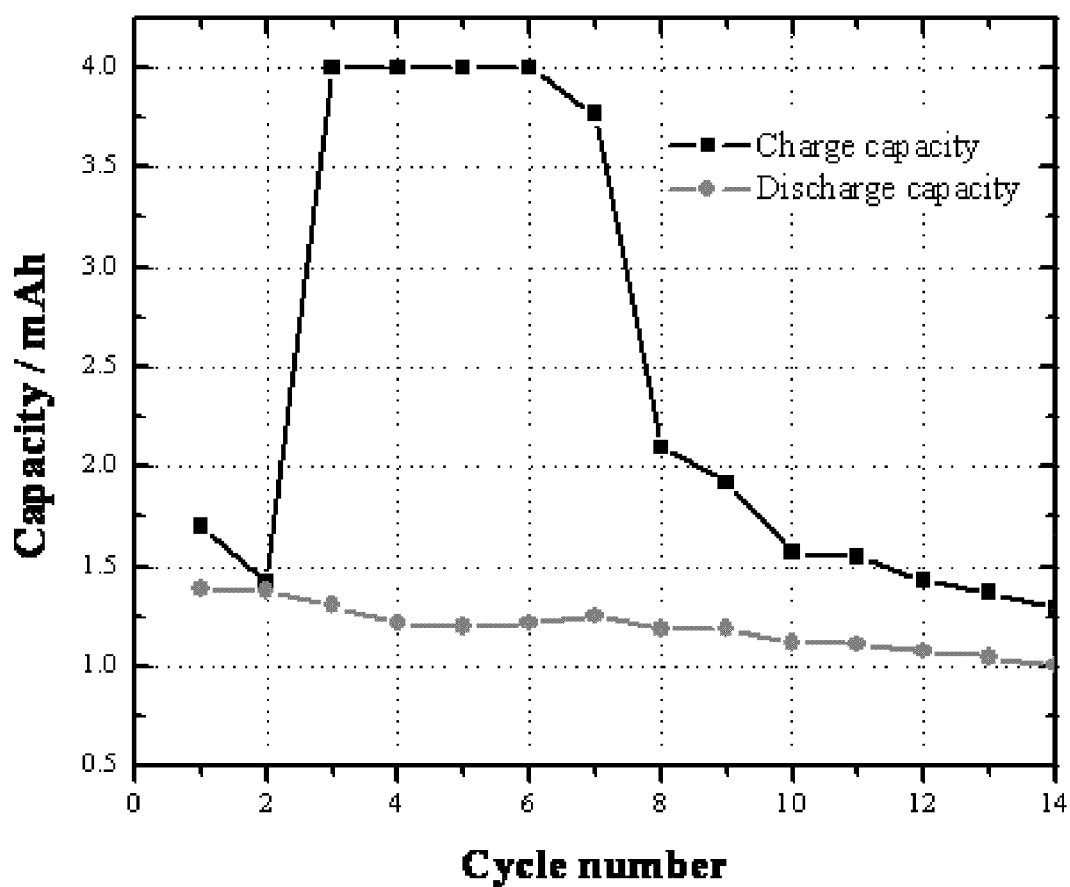
FIG. 3 is a graph of capacity vs. cycle number for a $Li_{1.2}Ni_{0.15}Co_{0.1}Mn_{0.55}O_2$/MCMB cell containing 5 wt % tetraethyl 2,5-di-tert-butyl-1,4-phenylene diphosphate, according to one embodiment.

Capacity vs. cycle number graphs were also recorded for $Li_{1.2}Ni_{0.15}Co_{0.1}Mn_{0.55}O_2$/MCMB cells containing a shuttle of 5 wt % tetraethyl 2,5-di-tert-butyl-1,4-phenylene diphosphate in an electrolyte of 1.2 M $LiPF_6$ in EC/EMC (3:7 by weight), at a charging rate of C/10. See FIG. 3. It is believed that the difference between the charge capacity and discharge capacity represents the charge that is carried by redox shuttle. During each cycle, about 200% capacity was shunted by redox shuttle and the overcharge rate is 300%.

Example 5

Figure 4:
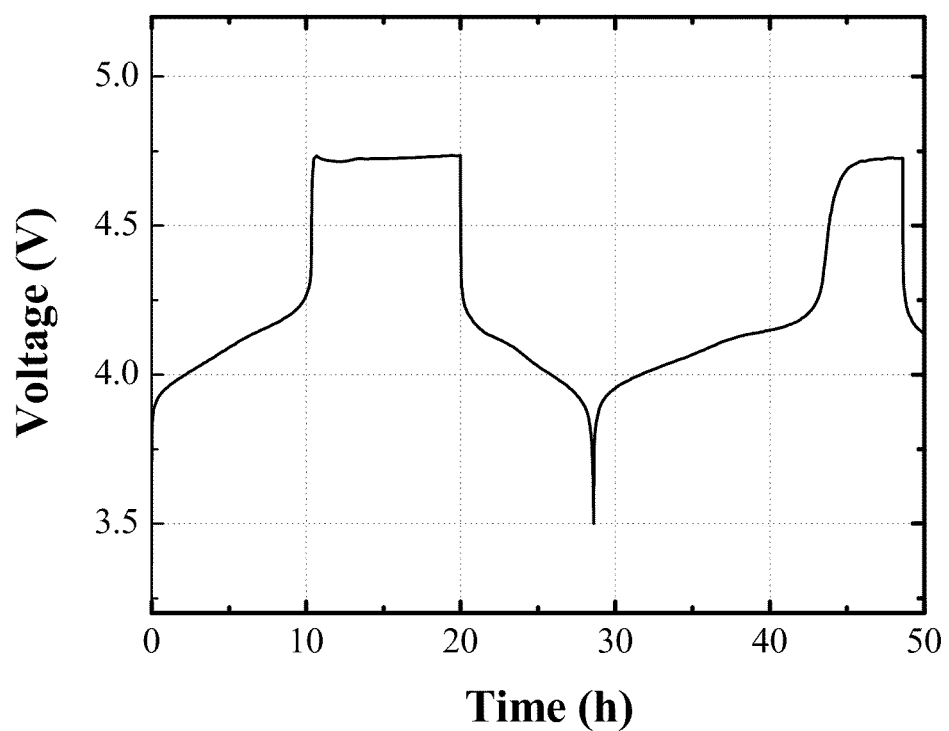
FIG. 4 is a graph of cell potential vs. time for a spinel $LiMn_2O_4$/Li cell containing 5 wt % tetraethyl 2,5-di-tert-butyl-1,4-phenylene diphosphate, according to one embodiment.

Cell potential vs. time was recorded for a spinel $LiMn_2O_4$/Li cell containing a shuttle of 5 wt % tetraethyl 2,5-di-tert-butyl-1,4-phenylene diphosphate in an electrolyte of 1.2 M $LiPF_6$ in EC/EMC (3:7 by weight), at a charging rate of C/10. See FIG. 4. The cell was charged at a C/10 rate for 20 hours, and then discharged at a C/10 rate to 3.5 V. During the first 10 hours of testing, the normal charging plateau for the spinel $LiMn_2O_4$/Li cell is observed at about 4.1 V. Once the cell was fully charged, the potential rises rapidly to about 4.8 V, where the shuttle is activated and carries the current through the lithium-ion cells. Therefore, the cell voltage is nearly invariant under the help of the redox shuttle added otherwise the cell voltage would rise rapidly until triggering electrochemical reaction of the cell components. After the 20 hours charging period, the current was reversed and the cell was discharged to a cutoff voltage of 2.0 V.

Example 6

Figure 5:
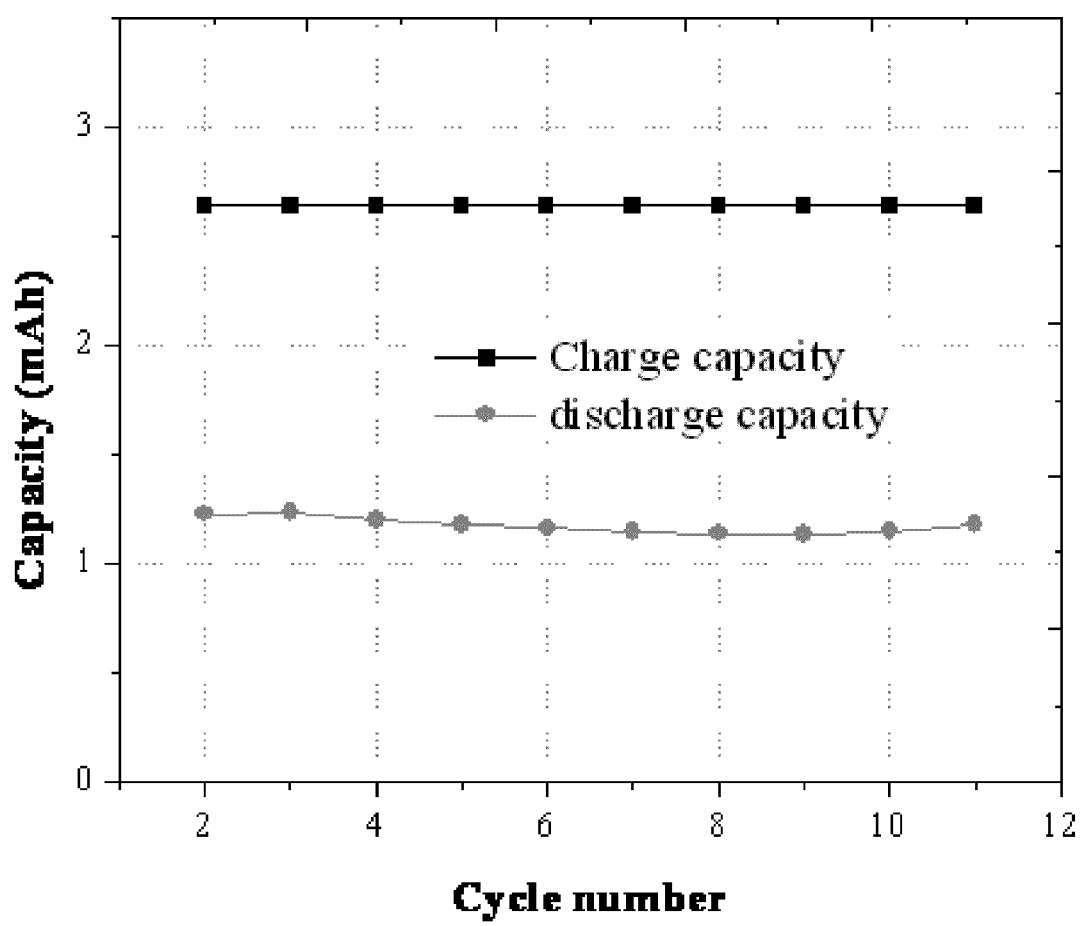
FIG. 5 is a graph of capacity vs. cycle number for spinel LiMn2O4/Li cell containing 5 wt % tetraethyl 2,5-di-tert-butyl-1,4-phenylene diphosphate, according to one embodiment.

Capacity vs. cycle number was recorded for a spinel $LiMn_2O_4$/Li cell containing a shuttle of 5 wt % tetraethyl 2,5-di-tert-butyl-1,4-phenylene diphosphate in an electrolyte of 1.2 M $LiPF_6$ in EC/EMC (3:7 by weight), at a charging rate of C/10. See FIG. 5. The difference between the charge capacity and discharge capacity was the extra electricity that carried by redox shuttle additive. During each cycle, about 100% capacity was shunted by redox shuttle and the overcharge rate is 200%.

Example 7

Figure 6:
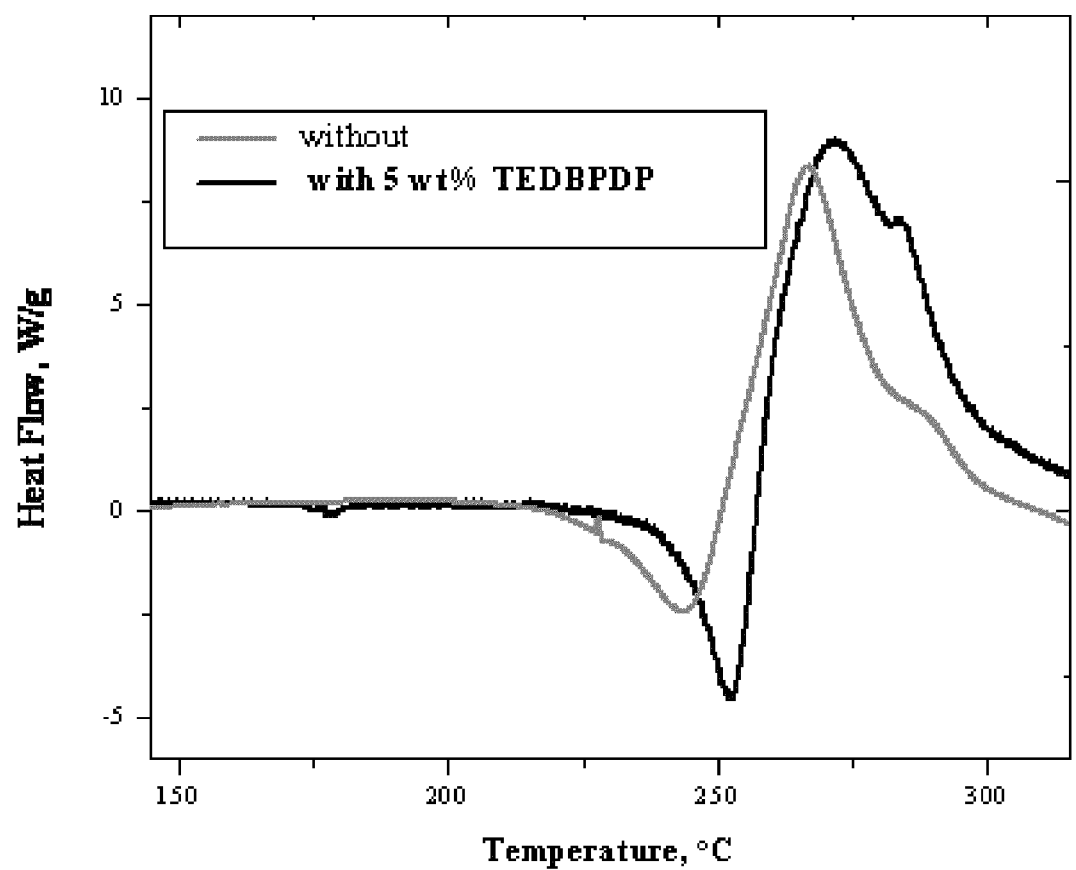
FIG. 6 is a graph of DSC profiles of electrolytes 1.2 M $LiPF_6$ in EC/EMC (3:7 by weight) without and with 5 wt % tetraethyl 2,5-di-tert-butyl-1,4-phenylene diphosphate, according to various embodiment.

DSC profiles of the electrolyte 1.2 M $LiPF_6$ in EC/EMC (3:7 by weight) without and with a redox shuttle of 5 wt % tetraethyl 2,5-di-tert-butyl-1,4-phenylene diphosphate were recorded. See FIG. 6. Upon addition of the redox shuttle, the main degradation peak of the electrolyte at 265° C. was shifted to 272° C., thereby indicating a fire retardant effect of the shuttle.

What is claimed is:

1. An electrolyte comprising:
    an alkali metal salt;
    a polar aprotic solvent; and
    a redox shuttle;
    wherein:
        the redox shuttle comprises an aromatic compound represented by Formula I, II, III, or IV:

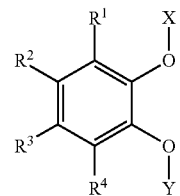

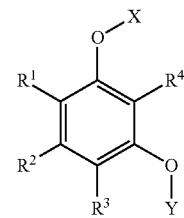

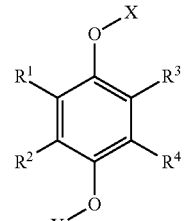

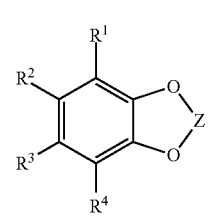

wherein:
   $R^1, R^2, R^3$, and $R^4$ are independently H, a alkyl group, a phosphate group, or a polyether group; or $R^1$ and $R^4$ are individually an alkyl group, and $R^2$ and $R^3$ are H or F; or $R^1$ and $R^3$ are individually an alkyl group, and $R^2$ and $R^4$ are H or F; or $R^1$ and $R^2$, or $R^2$ and $R^3$; or $R^3$ and $R^4$ join together to form a fused ring on the benzene ring;

X and Y are independently a group of Formula (A):

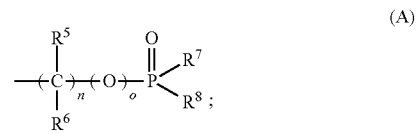

Z is a group of Formula (B):

$R^5$ and $R^6$ are independently H, F, Cl, Br, CN, $NO_2$ alkyl, a haloalkyl, phosphate, or polyether;

$R^7$ and $R^8$ are independently H, F, Cl, Br, CN, $NO_2$, alkyl, alkoxy, haloalkyl, haloalkoxy, aryl, aryloxy, haloaryl, haloaryloxy, or polyether;

$R^9$ is H, F, Cl, Br, CN, $NO_2$, alkyl, alkoxy, haloalkyl, haloalkoxy, aryl, aryloxy, haloaryl, haloaryloxy, or polyether;

n is an integer from 0 to 8; and p is 0 or 1;

with the proviso that where n is 0, p is 0, and where n is from 1 to 8, p is 0 or 1;

and the electrolyte is substantially non-aqueous.

2. The electrolyte of claim 1, wherein $R^1$, $R^2$, $R^3$, and $R^4$ are independently H, a alkyl group, or a polyether group.

3. The electrolyte of claim 1, wherein $R^1$, $R^2$, $R^3$, and $R^4$ are independently H, or a $C_1$-$C_4$ alkyl group.

4. The electrolyte of claim 1, wherein $R^1$ and $R^4$ are the same and are different from that of $R^2$ and $R^3$.

5. The electrolyte of claim 1, wherein $R^1$ and $R^3$ are the same and are different from that of $R^2$ and $R^4$.

6. The electrolyte of claim 1, wherein $R^1$ and $R^4$ are individually an alkyl group, and $R^2$ and $R^3$ are H.

7. The electrolyte of claim 1, wherein $R^1$ and $R^4$ are individually methyl, ethyl, n-propyl, iso-propyl, n-butyl, sec-butyl, or tert-butyl.

8. The electrolyte of claim 1, wherein $R^1$ and $R^3$ are individually an alkyl group, and $R^2$ and $R^4$ are H.

9. The electrolyte of claim 1, wherein $R^1$ and $R^3$ are individually methyl, ethyl, n-propyl, iso-propyl, n-butyl, sec-butyl, or tert-butyl.

10. The electrolyte of claim 1, where the redox shuttle comprises:

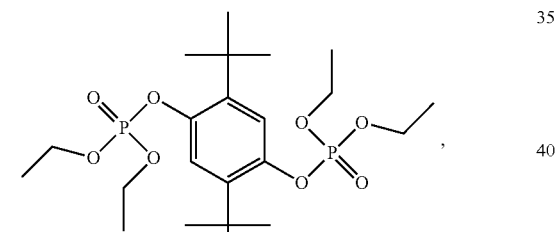,

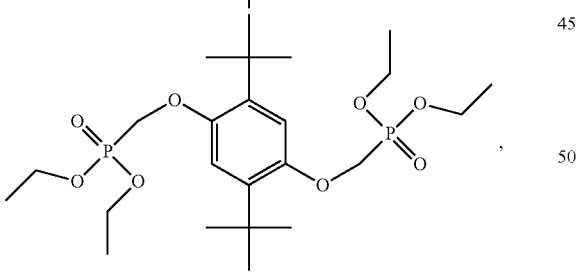,

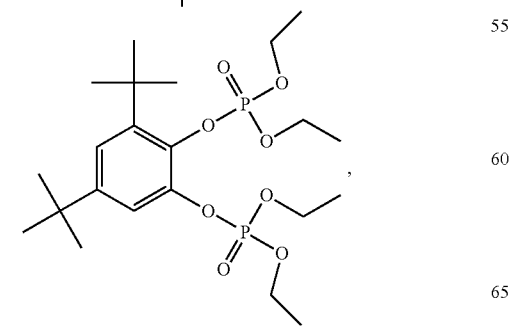,

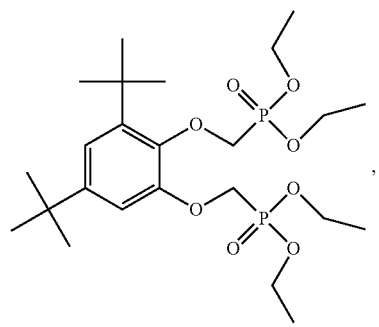,

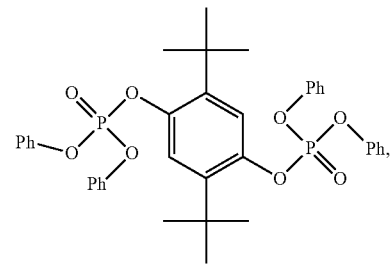,

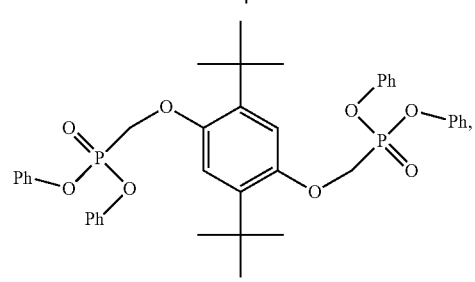,

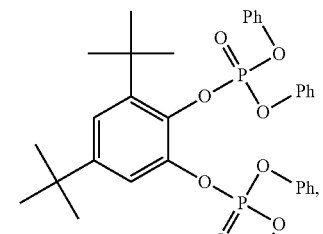,

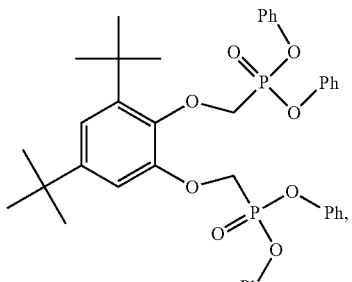,

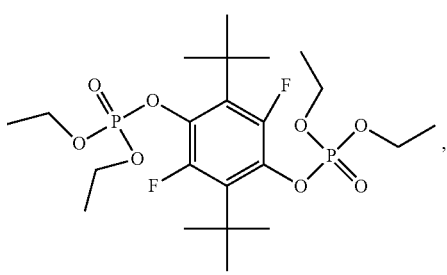,

-continued

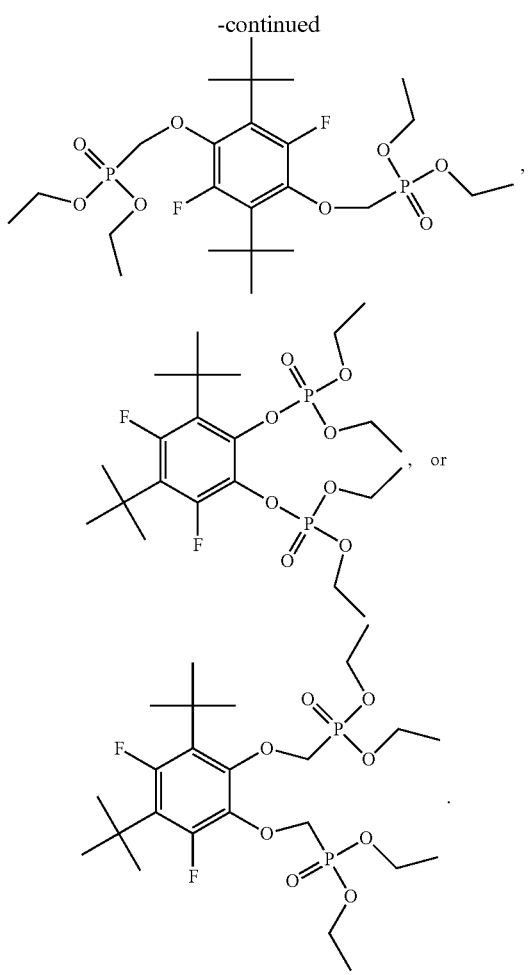

11. The electrolyte of claim 1, wherein the redox shuttle has a redox potential of 4 to 5 V in the electrolyte.

12. The electrolyte of claim 1, wherein the redox shuttle has two, three or four oxygen atoms.

13. The electrolyte of claim 1, wherein a concentration of the redox shuttle in the electrolyte is from 0.0005 wt % to 50 wt %.

14. The electrolyte of claim 1, wherein the alkali metal salt comprises a lithium salt.

15. The electrolyte of claim 14, wherein the alkali metal salt comprises Li[(C$_2$O$_4$)$_2$B], Li(C$_2$O$_4$)BF$_2$, LiClO$_4$, LiBF$_4$, LiAsF$_6$, LiPF$_6$, LiCF$_3$SO$_3$, Li(CF$_3$SO$_2$)$_2$N, Li(CF$_3$SO$_2$)$_3$C, LiN(SO$_2$C$_2$F$_5$)$_2$, or a lithium alkyl fluorophosphate.

16. The electrolyte of claim 1, wherein the polar aprotic solvent comprises ethylene carbonate, propylene carbonate, dimethyl carbonate; ethyl methyl carbonate; diethyl carbonate; methyl propyl carbonate; ethyl propyl carbonate; dipropyl carbonate; bis(trifluoroethyl)carbonate; bis(pentafluoropropyl)carbonate; trifluoroethyl methyl carbonate; pentafluoroethyl methyl carbonate; heptafluoropropyl methyl carbonate; perfluorobutyl methyl carbonate; trifluoroethyl ethyl carbonate; pentafluoroethyl ethyl carbonate; heptafluoropropyl ethyl carbonate; perfluorobutyl ethyl carbonate; fluorinated oligomers; dimethoxyethane; triglyme; dimethylvinylene carbonate; tetraethyleneglycol; dimethyl ether; polyethylene glycols; sulfones; or γ-butyrolactone.

17. An electrochemical device comprising
a cathode
an anode; and
an electrolyte comprising:
  an alkali metal salt;
  a polar aprotic solvent; and
  a redox shuttle;
wherein:
  the redox shuttle comprises an aromatic compound represented by Formula I, II, III, or IV:

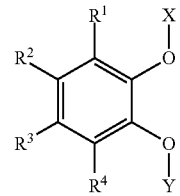

I

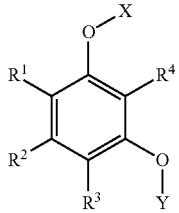

II

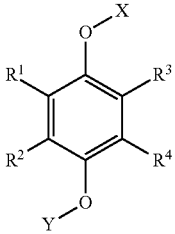

III

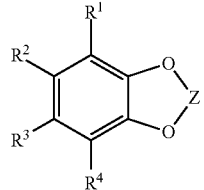

IV wherein:
  $R^1$, $R^2$, $R^3$, and $R^4$ are independently H, a alkyl group, a phosphate group, or a polyether group; or $R^1$ and $R^4$ are individually an alkyl group, and $R^2$ and $R^3$ are H or F; or $R^1$ and $R^3$ are individually an alkyl group, and $R^2$ and $R^4$ are H or F; or $R^1$ and $R^2$, or $R^2$ and $R^3$; or $R^3$ and $R^4$ join together to form a fused ring on the benzene ring;

X and Y are independently a group of Formula (A):

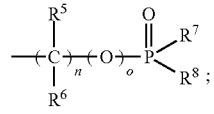

(A)

Z is a group of Formula (B):

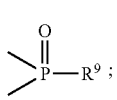

$R^5$ and $R^6$ are independently H, F, Cl, Br, CN, $NO_2$, alkyl, a haloalkyl, phosphate, or polyether;

$R^7$ and $R^8$ are independently H, F, Cl, Br, CN, $NO_2$, alkyl, alkoxy, haloalkyl, haloalkoxy, aryl, aryloxy, haloaryl, haloaryloxy, or polyether;

$R^9$ is H, F, Cl, Br, CN, $NO_2$, alkyl, alkoxy, haloalkyl, haloalkoxy, aryl, aryloxy, haloaryl, haloaryloxy, or polyether;

n is an integer from 0 to 8; and p is 0 or 1;

with the proviso that where n is 0, p is 0, and where n is from 1 to 8, p is 0 or 1; and the electrolyte is substantially non-aqueous.

18. A compound which is:

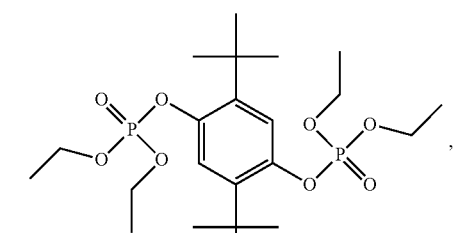

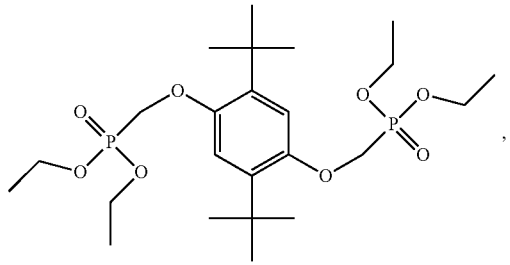

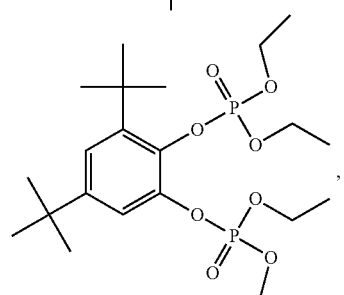

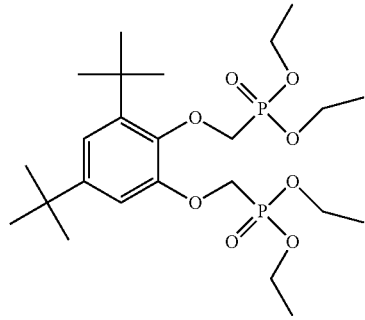

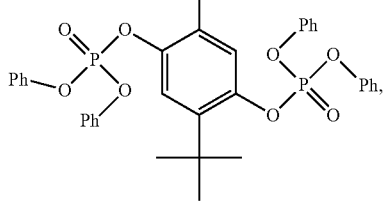

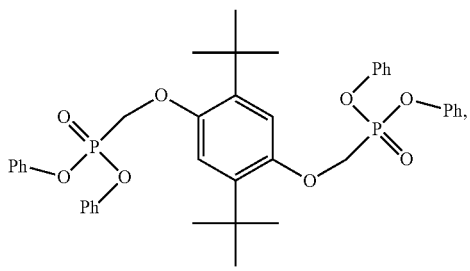

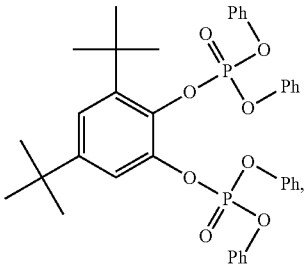

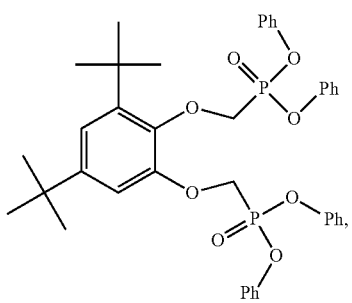

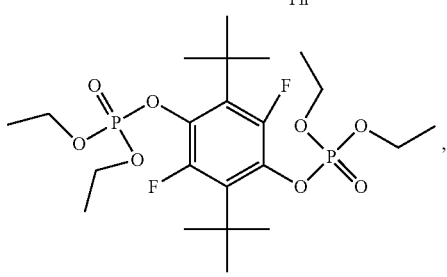

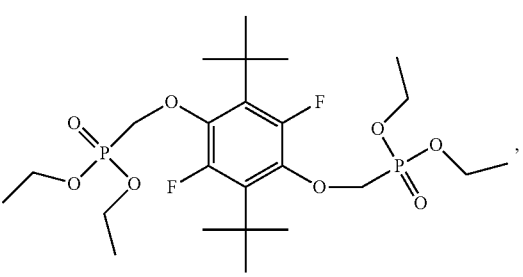

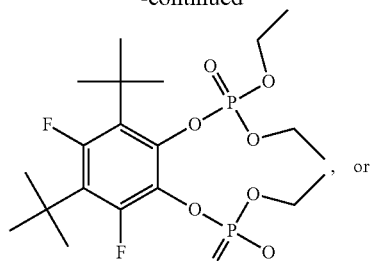
, or
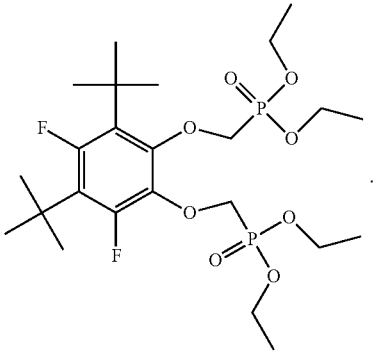
.
* * * * *

UNITED STATES PATENT AND TRADEMARK OFFICE
CERTIFICATE OF CORRECTION

PATENT NO.        : 8,968,940 B2
APPLICATION NO.   : 13/114468
DATED             : March 3, 2015
INVENTOR(S)       : Lu Zhang et al.

Page 1 of 1

It is certified that error appears in the above-identified patent and that said Letters Patent is hereby corrected as shown below:

IN THE CLAIMS

In Column 22, Claim 1, Lines 50-55, replace Structure (A) with:

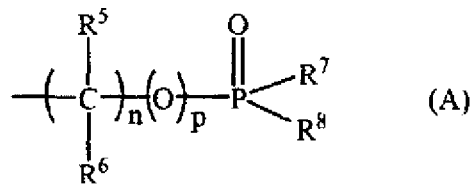

Signed and Sealed this
Sixteenth Day of June, 2015

Michelle K. Lee
*Director of the United States Patent and Trademark Office*